United States Patent [19]

DiNinno et al.

[11] Patent Number: 5,328,904
[45] Date of Patent: Jul. 12, 1994

[54] 2-PHENANTHRIDINYL CARBAPENEM ANTIBACTERIAL AGENTS

[75] Inventors: Frank P. DiNinno, Old Bridge; Mark L. Greenlee, Rahway; Thomas A. Rano, Somerville, all of N.J.; Wendy Lee, Chicago, Ill.

[73] Assignee: Merck & Co., Inc., Rahway, N.J.

[21] Appl. No.: 9,622

[22] Filed: Jan. 27, 1993

[51] Int. Cl.$^5$ .................. C07D 487/00; A01N 43/00; A61K 31/395
[52] U.S. Cl. ..................................... 514/210; 540/302
[58] Field of Search .................. 540/302; 514/210

[56] References Cited

U.S. PATENT DOCUMENTS

| | | |
|---|---|---|
| 4,260,627 | 4/1981 | Christensen et al. ............... 424/274 |
| 4,465,632 | 8/1984 | Christensen et al. ............. 260/245.2 |
| 4,543,257 | 9/1985 | Cama et al. ....................... 514/210 |
| 4,978,659 | 8/1989 | Salzmann et al. . |
| 5,004,739 | 4/1991 | Salzmann et al. . |
| 5,004,740 | 4/1991 | Salzmann et al. . |
| 5,006,519 | 4/1991 | Dininno et al. . |
| 5,011,832 | 4/1991 | Salzmann et al. . |
| 5,034,385 | 7/1991 | Dininno et al. . |
| 5,037,820 | 8/1991 | Dininno et al. . |
| 5,132,422 | 7/1991 | Dininno et al. . |
| 5,153,185 | 10/1992 | Dininno et al. . |
| 5,157,033 | 10/1992 | Dininno et al. . |
| 5,162,314 | 11/1992 | Dininno et al. . |

FOREIGN PATENT DOCUMENTS 0277743 8/1988 European Pat. Off. .
0444889 2/1991 European Pat. Off. .

OTHER PUBLICATIONS

L. D. Cama et al., Total Synthesis of Theinamycin Analgos-III, Tetrahedron 39, 2531 (1983).
R. N. Guthikonda et al., Structure Activity Relationships in the 2-Arylcarbapenem Series, J. Med. Chem., 30, 871 (1987).

Primary Examiner—Marianne M. Cintins
Assistant Examiner—Rebecca Cook
Attorney, Agent, or Firm—Joseph F. DiPrima; Mark R. Daniel; David A. Muthard

[57] ABSTRACT

The present invention relates to antibacterial agents of the carbapenem class, in which the 2-position sidechain is characterized by a phenanthridine moiety, substituted by various neutral substituents.

16 Claims, No Drawings

2-PHENANTHRIDINYL CARBAPENEM ANTIBACTERIAL AGENTS

BACKGROUND OF THE INVENTION

The present invention relates to antibacterial agents of the carbapenem class, in which the 2-position sidechain is characterized by a phenanthridine moiety, substituted by various neutral substituents, as described in more detail further below.

Thienamycin was an early carbapenem antibacterial agent having a broad spectrum; it has the following formula:

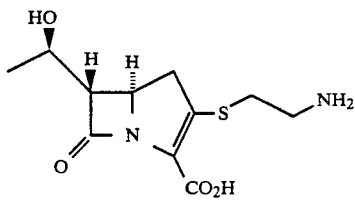

Later, N-formimidoyl thienamycin was discovered; it has the formula:

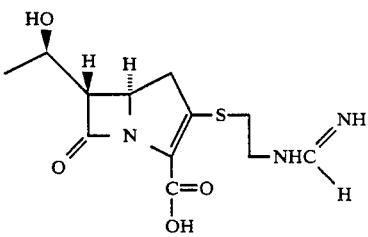

The 2-phenanthridinyl-carbapenems of the present invention are not characterized by a broad antibacterial spectrum such as that of thienamycin or N-formimidoyl thienamycin. Rather, their spectrum of activity is largely limited to gram positive microorganisms, especially methicillin resistant *Staphylococcus aureus* (MRSA), methicillin resistant *Staphylococcus epidermidis* (MRSE), and methicillin resistant coagulase negative Staphylococci (MRCNS). The antibacterial compounds of the present invention thus comprise an important contribution to therapy of these difficult to control pathogens. Moreover, there is an increasing need for agents effective against such pathogens (MRSA/MRCNS) which are at the same time safe, i.e., free from undesirable toxic side effects. No β-lactam antibacterial has yet been found which meets these requirements. And, the current agent of choice, vancomycin, a glycopeptide antibacterial, is experiencing an ever increasing amount of resistance in the MRSA/MRCNS pathogens.

More recently, carbapenem antibacterial agents have been described which have a 2-substituent which is an aryl moiety optionally substituted by, e.g., aminomethyl and substituted aminomethyl. These agents are described in U.S. Pat. Nos. 4,543,257 and 4,260,627 and have the formula:

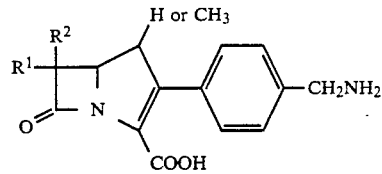

However, there is no description or suggestion of a phenanthridinyl 2-substituent such as characterizes the compounds of the present invention, nor is there any suggestion of the suprisingly better anti-MRSA/MRCNS activity of the compounds of the present invention.

EP-A-0277 743 describes a particular class of compounds of the formula:

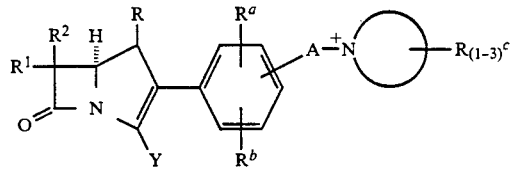

but this limited teaching in no way suggests the totally different compounds of the present invention, nor their surprisingly better anti-MRSA/MRCNS activity.

Recently patents have issued disclosing the 2-substituted carbapenems having anti-MRSA/MRCNS activity (see U.S. Pat. Nos. 5,004,739; 5,004,740; 5,011,832; 5,025,008; 5,032,587; 5,132,422; 5,025,007 and 5,034,384, all assigned to Merck & Co., Inc.). However, there is no published description of or suggestion of a substituted carbapenem having a phenanthridinyl 2-substituent such as characterizes the compounds of the present invention.

SUMMARY OF INVENTION

The present invention provides novel carbapenem compounds of the formula:

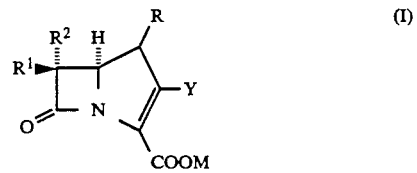

(I)

wherein

Y is a)

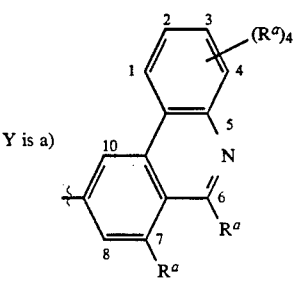

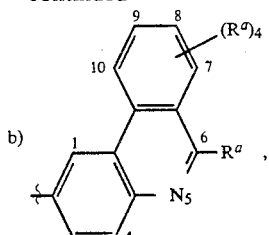

b)

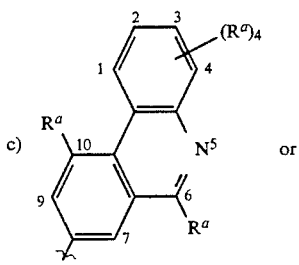

c) or

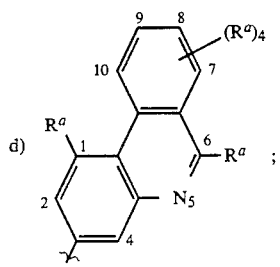

d)

R is H or CH$_3$;

R$^1$ and R$^2$ are independently H, CH$_3$—, CH$_3$CH$_2$—, (CH$_3$)$_2$CH—, HOCH$_2$—, CH$_3$CH(OH)—, (CH$_3$)$_2$C(OH)—, FCH$_2$CH(OH)—, F$_2$CHCH(OH)—, F$_3$CCH(OH)—, CH$_3$CH(F)—, CH$_3$CF$_2$—, or (CH$_3$)$_2$C(F)—;

R$^a$ are independently selected from the group consisting of hydrogen and the radicals set out below, provided that not more than four R$^a$ radicals are other than hydrogen:

a) a trifluoromethyl group: —CF$_3$;
b) a halogen atom: —Br, —Cl, —F, or —I;
c) C$_1$-C$_4$ alkoxy radical: —OC$_{1-4}$ alkyl, wherein the alkyl is optionally mono-substituted by R$^q$, where R$^1$ is a member selected from the group consisting of —OH, —OCH$_3$, —CN, —C(O)NH$_2$, —OC(O)NH$_2$, CHO, —C(O)N(CH$_3$)$_2$, —SO$_2$NH$_2$, —SO$_2$N(CH$_3$)$_2$, —SOCH$_3$, —SO$_2$CH$_3$, —F, —CF$_3$, —COOM$^a$ (where M$^a$ is hydrogen, alkali metal, methyl or phenyl), tetrazolyl (where the point of attachment is the carbon atom of the tetrazole ring and one of the nitrogen atoms is mono-substituted by M$^a$ as defined above) and —SO$_3$M$^b$ (where M$^b$ is hydrogen or an alkali metal);

d) a hydroxy group: —OH;
e) a carbonyloxy radical: —O(C=O)R$^s$, where

R$^s$ is C$_{1-4}$ alkyl or phenyl, each of which is optionally mono-substituted by R$^q$ as defined above;

f) a carbamoyloxy radical: —O(C=O)N(R$^y$)R$^z$ where

R$^y$ and R$^z$ are independently H, C$_{1-4}$ alkyl (optionally mono-substituted by R$^q$ as defined above), together a 3- to 5-membered alkylidene radical to form a ring (optionally substituted with R$^q$ as defined above) or together a 2- to 4-membered alkylidene radical, interrupted by —O—, —S—, —S(O)— or —S(O)$_2$— to form a ring (where the ring is optionally mono-substituted with Rq as defined above);

g) a sulfur radical: —S(O)$_n$—R$^s$ where n=0-2, and R$^s$ is defined above;

h) a sulfamoyl group: —SO$_2$N(R$^y$)R$^z$ where R$^y$ and R$^z$ are as defined above;

i) azido: N$_3$ j) a formamido group: —N(R$^f$)(C=O)H, where R$^f$ is H or C$_{1-4}$ alkyl, and the alkyl thereof is optionally mono-substituted by R$^q$ as defined above;

k) a (C$_1$-C$_4$ alkyl)carbonylamino radical: —N(R$^f$)(C=O)C$_{1-4}$ alkyl, where R$^f$ is as defined above, and the alkyl group is also optionally mono-substituted by R$^q$ as defined above;

l) a (C$_1$-C$_4$ alkoxy) carbonylamino radical: —N(R$^f$)(C=O)OC$_{1-4}$ alkyl, where R$^f$ is as defined above, and the alkyl group is also optionally mono-substituted by R$^q$ as defined above;

m) a ureido group: —N(R$^f$)(C=O)N(R$^y$)R$^z$ where R$^f$, R$^y$ and R$^z$ are as defined above;

n) a sulfonamido group: —N(R$^f$)SO$_2$R$^s$, where R$^s$ and R$^f$ are as defined above;

o) a cyano group: —CN;

p) a formyl or acetalized formyl radical: —(C=O)H or —CH(OCH$_3$)$_2$;

q) (C$_1$-C$_4$ alkyl)carbonyl radical wherein the carbonyl is acetalized: —C(OCH$_3$)$_2$C$_{1-4}$ alkyl, where the alkyl is optionally mono-substituted by R$^q$ as defined above;

r) carbonyl radical: —(C=O)R$^s$, where R$^s$ is as defined above;

s) a hydroximinomethyl radical in which the oxygen or carbon atom is optionally substituted by a C$_1$-C$_4$ alkyl group: —(C=NOR$^z$)R$^y$ where R$^y$ and R$^z$ are as defined above, except they may not be joined together to form a ring; —(C=O)OC$_{1-4}$ alkyl, where the alkyl is optionally mono-substituted by R$^q$ as defined above;

u) a carbamoyl radical: —(C=O)N(R$^y$)R$^z$ where R$^y$ and R$^z$ are as defined above;

v) an N-hydroxycarbamoyl or N(C$_1$-C$_4$alkoxy)carbamoyl radical in which the nitrogen atom may be additionally substituted by a C$_1$-C$_4$ alkyl group: —(C=O)—N(OR$^y$)R$^z$ where R$^y$ and R$^z$ are as defined above, except they may not be joined together to form a ring;

w) a thiocarbamoyl group: —(C=S)N(R$^y$)(R$^z$) where R$^y$ and R$^z$ are as defined above;

x) carboxyl: —COOM$^b$, where M$^b$ is as defined above;

y) thiocyanate: —SCN;

z) trifluoromethylthio: —SCF$_3$;

aa) tetrazolyl, where the point of attachment is the carbon atom of the tetrazole ring and one of the nitrogen atoms is mono-substituted by hydrogen, an alkali metal or a C$_1$-C$_4$ alkyl optionally substituted by R$^q$ as defined above;

ab) an anionic function selected from the group consisting of: phosphono [P=O(OM$^b$)$_2$]; alkylphosphono {P=O(OM$^b$)-[O(C$_1$-C$_4$ alkyl)]}; alkylphosphinyl [P=O(OM$^b$)-(C$_1$-C$_4$ alkyl)]; phosphoramido [P=O(OM$^b$)N(R$^y$)R$^z$ and P=O(OM$^b$)NHR$^x$]; sulfino (SO$_2$M$^b$); sulfo (SO$_3$M$^b$); acylsulfonamides selected from the structures CONM$^b$SO$_2$R$^x$, CONM$^b$SO$_2$N(R$^y$)R$^z$, SO$_2$NM$^b$CON(R$^y$)R$^z$; and SO$_2$NM$^b$CN, where R$^x$ is phenyl or heteroaryl, where heteroaryl is a monocyclic aromatic hydrocarbon group having 5 or 6 ring atoms, in which a carbon atom is the point of attachment, in which one of the carbon atoms has been replaced by a nitrogen atom, in which one additional carbon atom is optionally replaced by a heteroatom selected from O or S, and in which from 1 to 2 additional carbon atoms are optionally replaced by a nitrogen heteroatom, and where the phenyl and heteroaryl are optionally mono-substituted by R$^q$, as defined above; M$^b$ is as defined above; and R$^y$ and R$^z$ are as defined above;

ac) C$_5$-C$_7$ cycloalkyl group in which one of the carbon atoms in the ring is replaced by a heteroatom selected from O, S, NH or N(C$_1$-C$_4$ alkyl) and in which one additional carbon atom may be replaced by NH or N(C$_1$-C$_4$ alkyl), and in which at least one carbon atom adjacent to each nitrogen heteroatom has both of its attached hydrogen atoms replaced by one oxygen thus forming a carbonyl moiety and there are one or two carbonyl moieties present in the ring;

ad) C$_2$-C$_4$ alkenyl radical, optionally mono-substituted by one of the substituents a) to ac) above and phenyl which is optionally substituted by R$^q$ as defined above;

ae) C$_2$-C$_4$ alkynyl radical, optionally mono-substituted by one of the substituents a) to ac) above;

af) C$_1$-C$_4$ alkyl radical;

ag) C$_1$-C$_4$ alkyl mono-substituted by one of the substituents a)-ac) above;

ah) a 2-oxazolidinonyl moiety in which the point of attachment is the nitrogen atom of the oxazolidinone ring, the ring oxygen atom is optionally replaced by a heteroatom selected from —S— and NR$^t$ (where R$^t$ is as defined above) and one of the saturated carbon atoms of the oxazolidinone ring is optionally mono-substituted by one of the substituents a) to ag) above;

M is selected from:
i) hydrogen;
ii) a pharmaceutically acceptable esterifying group or removable carboxyl protecting group; or
iii) an alkali metal or other pharmaceutically acceptable cation.

DETAILED DESCRIPTION OF THE INVENTION

The manufacture of compounds of Formula I may be carried out in a three-stage synthesis scheme followed by a final step which allows for the removal of any protecting groups. The objective of the first synthetic stage is to produce a base phenanthridine compound which may be converted to the two-position substituent of the carbapenem of Formula I. The objective of the second synthetic stage is to attach the base phenanthridine to the carbapenem. Finally, the objective of the third synthetic stage is to substitute the phenanthridine with the desired R$^a$. This third synthetic stage may be performed after the first synthetic stage or during or after the second synthetic stage according to the nature of the various R$^a$.

Flow Sheets A–E demonstrate alternative first stage syntheses. Flow Sheet F demonstrates a second stage synthesis. The third synthesis varies according to the selected R$^a$.

Referring to Flow Sheet A, 2-bromophenanthridine A-1, obtained by bromination of phenanthridine, was modified to the trimethylstannylphenanthridine A2. This is accomplished by reacting A1 with hexamethylditin in the presence of a palladium (O) catalyst such as tetrakis(triphenylphosphine)palladium and the like, and a phosphine, such as triphenylphosphine and the like, in a solvent such as toluene at an elevated temperature. The intermediate A2 may be incorporated in the synthesis of the compounds of the instant invention or it may be further modified.

Thus, the trimethylstannyl phenanthridine A2 may be oxidized by reacting A2 with an oxidizing agent such as m-chloroperbenzoic acid (MCPBA), magnesium monoperoxyphthalate (MMPP) and the like, optionally in the presence of a base such as sodium bicarbonate and the like. The resulting N-oxide A3 may be methylated to provide phenanthridine A4. Intermediate A4 may be reacted with a nucleophilic reagent, such as sodium cyanide, potassium cyanide, sodium methoxide, ammonia, methylamine and the like to provide the phenanthridine A5 having a substituent in the 6-position ( where R$^a$ in the 6-position is —OCH$_3$, —NH$_2$, —NHCH$_3$, —N(CH$_3$)$_2$, —CN, and the like)(L. Stephenson and W. K. Warburton, *J. Chem. Soc.* (C), 1355(1970)). Such an intermediate A5 may be incorporated in the synthesis of the compounds of the instant invention as described below, with or without modifying the R$^a$ substituent in the 6-position. For example the amine and substituted amine substituents may be utilized in the preparation of R$^a$ substituents j)–m) described hereinabove.

FLOW SHEET A

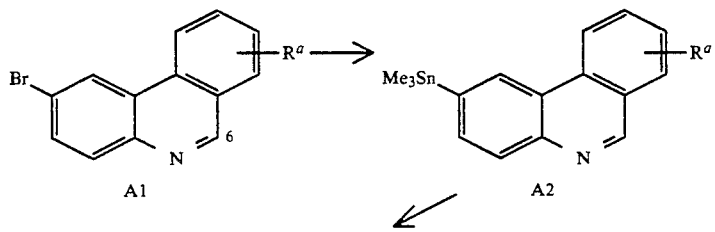

FLOW SHEET A
-continued

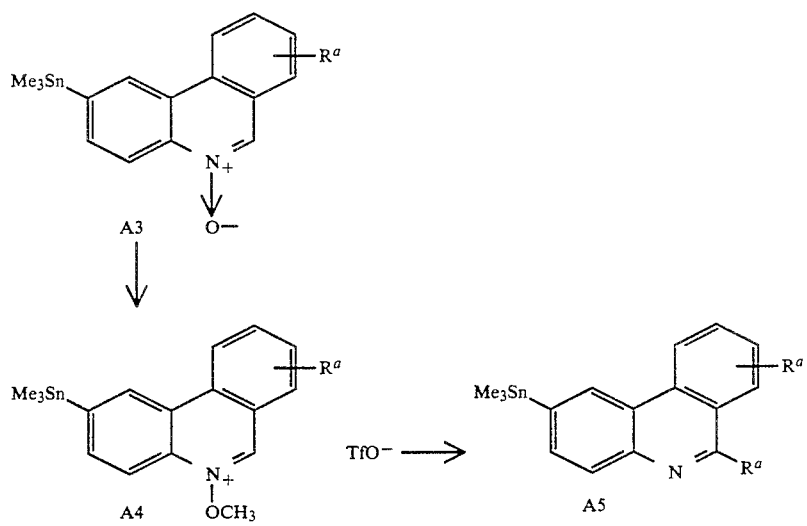

Alternatively, if the substitution pattern is not accessible from a commercially available phenanthridine, the substituted phenanthridine may be constructed from monocyclic components. Referring to Flow Sheets B and C this alternative synthesis can be generally described as a directed ortho metallation reaction to prepare starting materials required for a Suzuki cross-coupling reaction, ring closure to produce a suitably substituted phenanthridone and subsequent reductive dehalogenation to produce the desired phenanthridine platform. The first part of this suggested synthesis is utilized to produce similar phenanthridone and phenanthridine compounds by Snieckus, V., *Chem. Rev.* 1990, 90, 879–933; Fu. J. M. and Snieckus, V., *Tetrahedron Lett.* 1990, 31, p. 1665; Siddiqui, M. A., et al., *Tetrahedron Lett.*, Vol. 29, No. 43, 5463–5466 (1988); Mills, R. J., et al., *J. Org. Chem.*, 1989, 54, 4372–4385; Mills, R. J., *J. Org. Chem.*, 1989, 54, 4386–4390; and Suzuki, A., et al., *Synthetic Communications*, 11(7), 513–519 (1981).

Referring to Flow Sheet B compound, B-1 is substituted with a directed metallation group (DMG) by methods according to Snieckus, et al., above. The function of the directed metallation group (DMG) is to orchestrate adornment of the aromatic ring. It is highly desirable of the DMG that it also provide a precursor substituent for the necessary carboxy function or amino function forming the amide linkage of the object phenanthridone or the imine function of the object phenanthridine. Suitable DMG to serve as a carboxyl precursor are secondary and tertiary amides and oxazolino groups. Specifically, these precursors may be, for example, —CONEt$_2$, —CONHMe, 4,4-dimethyl-2-oxazolinyl, and the like. In the instance of compound B-1, DMG is of the carboxyl precursor type. Suitable DMG to serve as an amino precursor are protected primary and secondary amines. Specifically, these precursors may be —NH-tert-butoxycarbonyl (—NH-t-Boc), —NH-pivaloyl, phenylsulfonamido, and the like. Compound C-1 as described below is by way of example, substituted by a DMG of the amino precursor type.

As the first step of Flow Sheet B, the bromine of compound B-1 is protected through silylation via halogen metal exchange in the presence of TMS chloride at between about −100° to −50° C. to produce aryl silane B-2. Incorporation of an ortho substitutent R$^a$ or its appropriate precursor may be made on compound B-2 in accordance with standard directed metallation procedures described by Snieckus, et al., above. The resultant substituted aryl silane B-3 is ortho metallated and treated with an appropriate boron containing electrophile to obtain the requisite aryl boronic acid B-4. Suitable boron containing electrophiles include lower alkyl borates, such as trimethyl borate and tri-i-propyl borate. Alternatively, and not shown in the Flow Sheets, the ortho metallated compound may be treated with electrophiles such as trialkyltin halides providing the corresponding aryl stannanes which in turn are also useful intermediates in the production of biphenyls as reported by Stille, et al., *J. Am. Chem. Soc.*, 1987, Vol. 109, page 5478–5486. Preparation of biphenyl intermediate B-6 is accomplished in the Flow Sheets utilizing the Suzuki cross-coupling procedure and the appropriately adorned aryl compounds B-4 and B-5. The Suzuki coupling can be generally described as the reaction of an aryl boronic acid with an aryl halide or halide equivalent employing tetrakis(triphenylphosphine) palladium(O) catalyst in the presence of an aqueous solution of sodium carbonate in the solvents toluene/ethanol. The resulting biphenyl compound is isolated by standard methods. Compound B-5 may itself be produced by standard methods to obtain the halogen substitution, X', the amino moiety —NR'$_2$ and the desired substituents R$^a$ or their precursors. The preferred halogen X' is bromine, iodine or the halogen equivalent trifluoromethanesulfonyloxy. The preferred amino moiety, —NR'$_2$, may be any of —NO$_2$, —N$_3$, protected amine or amine. Biphenyl compound B-6 is subsequently transformed into the halogenated biphenyl B-7 via ipso substitution of the trimethylsilyl moiety in methylene chloride or other appropriate solvent employing iodine monochloride. Any number of halogenating reagents are suitable such IBr, NBS, I$_2$, Br$_2$, etc., which must be compatible with the already existing functionalities. The halogenated phenanthridone B-8 is obtained via transamidation of the amino moiety with the latent carboxy precursor in the form of DMG. Alternatively, the phenanthridone may be formed via transamidation of a biphenyl compound such as B-6 and the ipso substitution of the halogen performed upon the trimethylsilyl- phenanthridone.

The phenanthridone B-8 is subsequently transformed into the corresponding trimethylstannyl phenanthridine B-10. Such a transformation may be accomplished by reacting the phenanthridone B-8 with a halogenating agent such as phosphorous pentachloride, phosphorous oxychloride and the like to provide the halogenated phenanthridine B-9 (where X" is chloride, iodide and the like). The halogenated phenanthridine B-9 may then be treated with hexamethylditin in the presence of tetrakis(triphenylphosphine)palladium (O) and triphenylphosphine to provide the phenanthridine B-10.

Alternative syntheses of phenanthridones via a Beckmann Rearrangement are described by E. C. Homing et al. *J. Am. Chem. Soc.*, 74, 5153 (1952); H. L. Pan and T. L. Fletcher, *J. Heterocyclic Chem.*, 7, 313 (1970); H. L. Pan and T. L. Fletcher, *J. Heterocyclic Chem.*, 7, 597 (1970); H. L. Pan and T. L. Fletcher, *J. Med. Chem.*, 12, 822 (1969); and A. Guy and J.-P. Guette, *Synthesis*, 222 (1980). One Such synthetic route is illustrated in Examples 9 and 10.

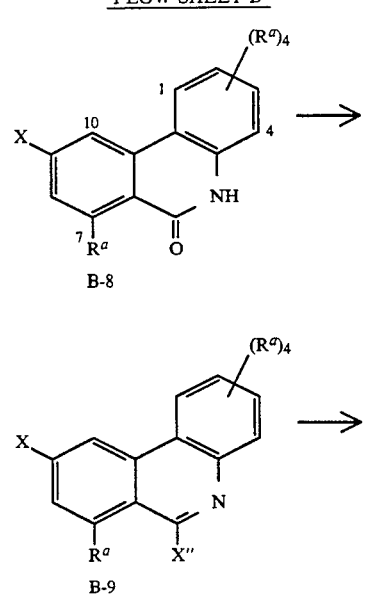

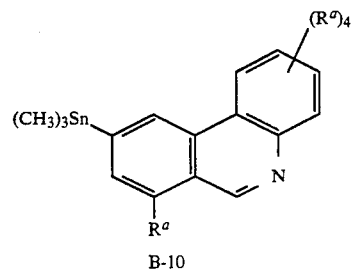

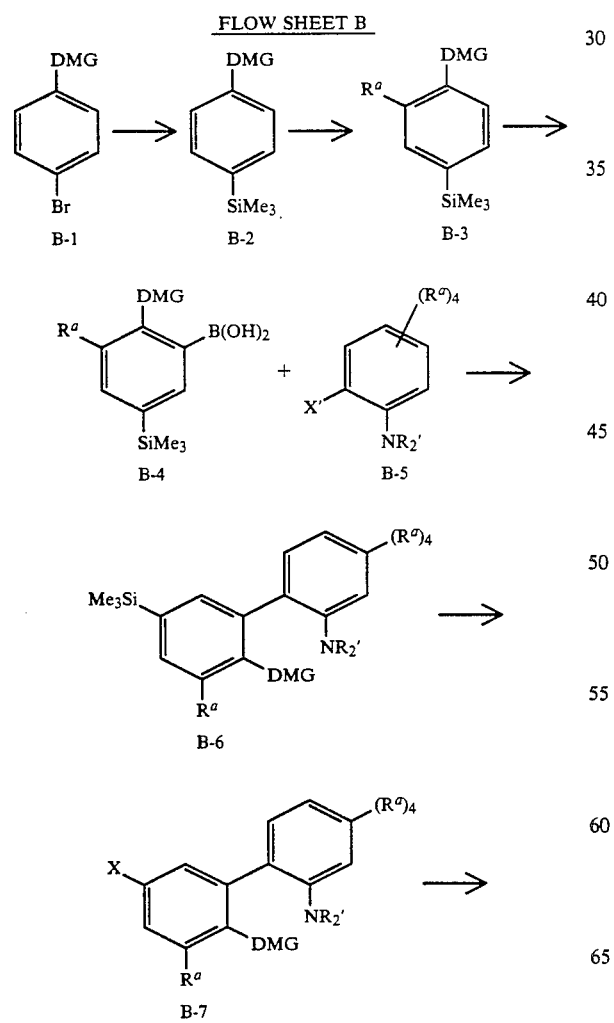

Referring to Flow Sheet C, the regioisomeric phenanthridine C-5, and subsequently the phenanthridine C-6, maybe produced in a manner analogous to that of phenanthridone B-8. Compound C1 is dissimilar to compound B-4 in that DMG of compound C1 is of the amino precursor type. Compound C1 is reacted with the appropriately adorned compound C2 to prepare biphenyl intermediate C3 utilizing the Suzuki cross-coupling procedure. As above biphenyl compound C3 is transformed into halogenated biphenyl C4 via ipso substitution and into phenanthridine C5 under acidic conditions. Conversion of the phenanthridine C5 into the phenanthridine C-6 may be accomplished by the method described herein above.

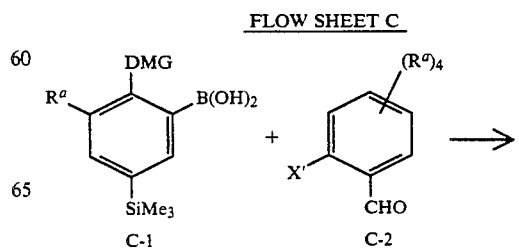

FLOW SHEET C -continued

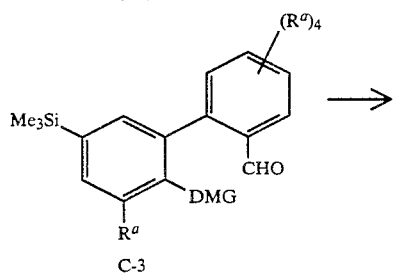
C-3

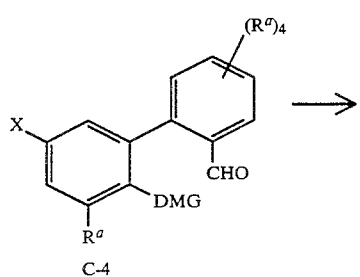
C-4

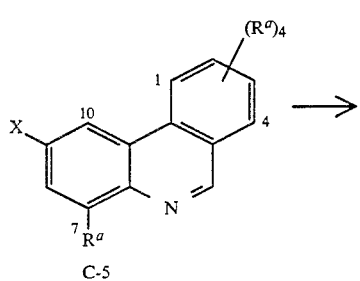
C-5

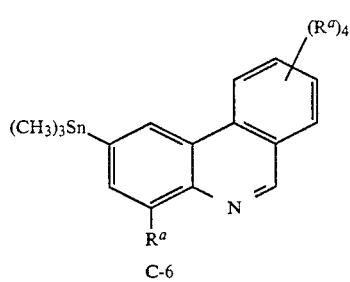
C-6

Referring to Flow Sheets D and E, the phenanthridines D-5 and E-6, having halogen group X in the 3-position (which will subsequently lead to attachment of the carbapenem nucleus at a different position on the phenanthridine moiety) may be similarly produced from starting materials analogous to those employed in Flow Sheet B and C.

Specifically referring to Flow Sheet D, compound D-1, wherein DMG represents an amino precursor and X' is a suitable leaving group, may be derived from readily available compounds, such as 5-bromo-2-hydroxyaniline and the like. Compound D-1 is reacted with a suitably substituted phenyl boronic acid D-2 via a Suzuki cross-coupling procedure to form the biphenyl compound D-3. The silyl moiety on compound D-3 is then replaced with a suitable halogen, such as bromine or iodine via ipso substitution. The halogenated biphenyl D-4 then is cyclized to form the desired phenanthridine D-5. This phenanthridine may be subsequently converted to the trimethylstannyl phenanthridine by the methods described herein above.

FLOW SHEET D

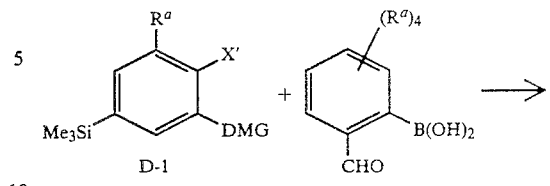
D-1    D-2

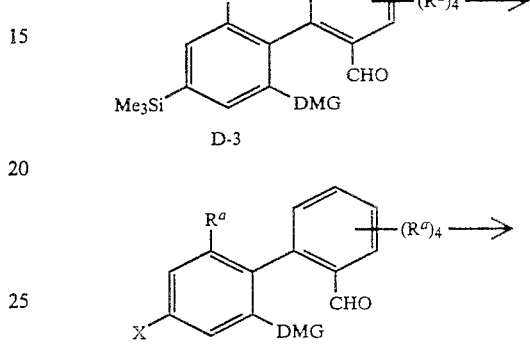
D-3

D-4

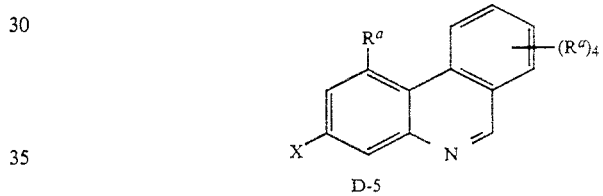
D-5

Specifically referring to Flow Sheet E, the starting material, compound E-1, may be derived from commercially available compounds, such as 5-bromo salicyclic acid and the like. Compound E-1 is reacted with the suitably substituted phenyl boronic acid E-2 via a Suzuki cross-coupling procedure to form the biphenyl compound E-3. The silyl moiety on Compound E-3 is transformed into a halogen moiety via ipso substitution. The halogenated biphenyl E-4 is then cyclized to form the phenanthridone E5 via transamidization. The phenanthridone intermediate may then be converted to the phenanthridine as previously described.

FLOW SHEET E

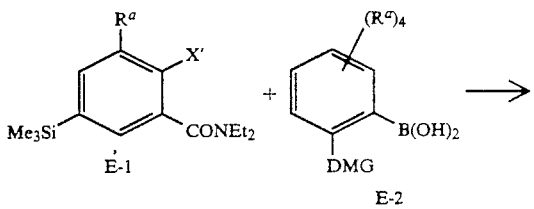
E-1    E-2

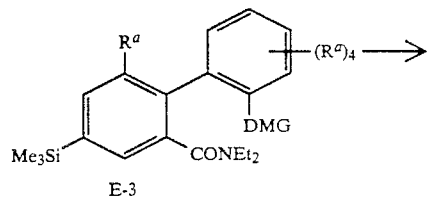
E-3

-continued
FLOW SHEET E

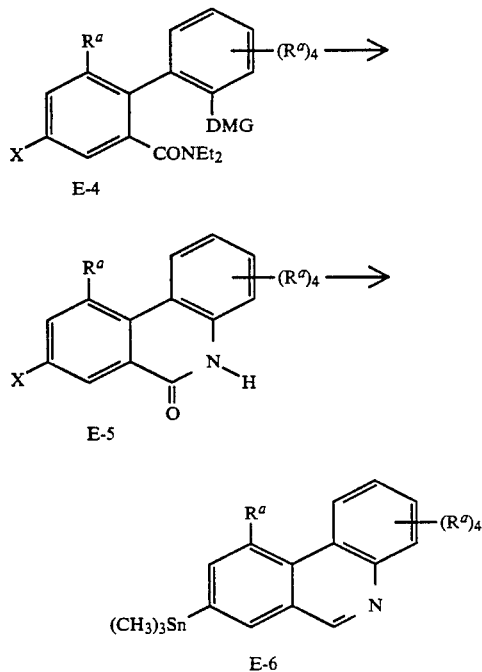

The object compounds of Flow Sheets A-E, the various regioisomeric phenanthridines, form the nucleus of the 2-position substitution of the carbapenem compounds taught herein. As such they are shown to be $R^a$ substituted. However, it is immediately clear to those skilled in the art that certain $R^a$ listed above, if substituted on B-3, B-5, or both (or the corresponding intermediates found in Flow Sheets A and C-E) would not survive or permit the synthesis to the phenanthridines. Thus, where a certain $R^a$ is desired, for example, on compound B-10 and this $R^a$ is not compatible with the synthesis scheme to produce B-10, then a compatible precursor substituent may be employed through the synthesis.

The identity of the precursor substituent employed is not crucial so long as it does not interfere with the synthesis to the phenanthridine and so long as it may be thereafter converted to more desireable substitution. Preferred precursor substituents are methyl, hydroxymethyl and protected hydroxymethyl.

Thus, for example as to the $R^a$ substituent on compound B-10, it may be an $R^a$ with or without protecting groups stable to the conditions of producing compound B-10 and stable to the conditions of subsequently adding B-10 to the carbapenem. Alternatively, it may be a stable precursor substituent which is stable to the conditions of making B-10, which is optionally stable to the conditions of adding B-10 to the carbapenem and which is convertible to a desired $R^a$ or to another precursor substituent.

As stated above, the second stage synthesis is to attach the base phenanthridine to the 2-position of the carbapenem.

Flow Sheet F shows a second stage synthesis, i.e. attachment of the base phenanthridine, such as B-10, to the 2-position of the carbapenem. This synthesis involves a palladium catalyzed cross-coupling reaction between a carbapenem triflate and a suitably substituted arylstannane, a process which is described in U.S. patent application No. 485,096 filed Feb. 26, 1990. Referring to Flow Sheet F, the 2-oxocarbapenam F-1 is reacted with a suitable trifluoromethanesulfonyl source, such as trifluoromethanesulfonic anhydride, trifluoromethanesulfonyl chloride and the like, in the presence of an organic nitrogen base, such as triethylamine, diisopropylamine and the like, in polar aprotic solvent, such as tetrahydrofuran or methylene chloride. The hydroxyl moiety may then be protected. Thus, optionally an organic nitrogen base, such as triethylamine and the like, is added to the reaction solution followed immediately by a silylating agent, such as trimethylsilyl trifluoromethanesulfonate to provide intermediate F2 where $R^p$ is an alkyl silyl group. Regardless of whether the hydroxyl moiety is left unprotected or is modified with a protecting group, an aprotic polar coordinating solvent, such as DMF, 1-methyl-2-pyrrolidinone and the like, is then added. This is followed by the addition of a palladium compound, such as tris(dibenzylideneacetone)dipalladiumchloroform, palladium acetate and the like, the stannane B-10 and optionally a suitably substituted phenylphosphine, such as tris(4-methoxyphenyl)phosphine, tris(2,4,6- trimethoxyphenyl)phosphine and the like. A halide source, such as lithium chloride, zinc chloride, tetrabutylammonium chloride, diisopropylamine hydrochloride, triethylamine hydrochloride and the like, is added and the reaction solution is allowed to warm and is stirred at a suitable temperature, such as 0° to 50° C. for from a few minutes to 7 days. The carbapenem F-3 is obtained by conventional isolation/purification methodology known in the art.

Generally speaking, the mild conditions of the synthesis shown in Flow Sheet F allow for a wide range of functional groups $R^a$ to be present. However, in certain cases it is advantageous for the $R^a$ substituent(s) of the stannane B-10 to be introduced in a protected or precursory form. Final elaboration of $R^a$ from a precursor substituent, e.g. hydroxymethyl, may be accomplished on carbapenem intermediate F-3. Removal of hydroxyl and carboxyl protecting groups then provides the final compound of Formula I. Such final elaboration and deprotection is described in further detail below.

FLOW SHEET F

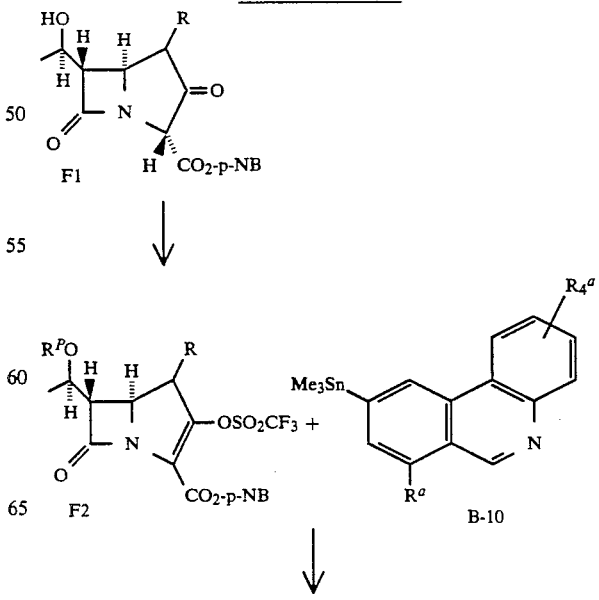

-continued
FLOW SHEET F

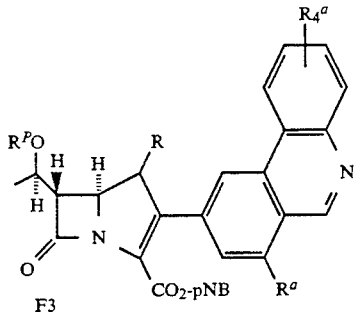

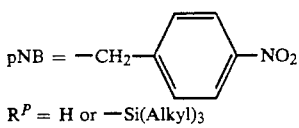

$R^P = H$ or $-Si(Alkyl)_3$

The steps for preparing the 2-oxocarbapenam intermediate F1 are well known in the art and are explained in ample detail by D. G. Melillo et al., *Tetrahedron Letters*, 21, 2783 (1980), T. Salzmann et al, *J. Am. Chem. Soc.*, 102, 6161 (1980), and L. M. Fuentes, I. Shinkai, and T. N. Salzmann, *J. Am. Chem. Soc.*, 108, 4675 (1986). The syntheses are also disclosed in U.S. Pat. No. 4,269,772, U.S. Pat. No. 4,350,631, U.S. Pat. No. 4,383,946 and U.S. Pat. No. 4,414,155 all assigned to Merck and Company, Inc.

The general synthesis description depicted above in the Flow Sheets $R^a$ shows a protected 1-hydroxyethyl substitution on the 6-position of the carbapenem. After final deprotection, a 1-hydroxyethyl substituent is obtained, which is preferred in most cases. However, it has been been found that with certain 2-position-sidechain selections, the ultimate balance of favorable properties in the overall molecule may be enhanced by selection of the 6-(1-fluoroethyl) moiety instead. Preparation of 6-fluoroalkyl compounds within the scope of the present invention is carried out in a straightforward manner using techniques well known in the art of preparing carbapenem antibacterial compounds. See, e.g., J. G. deVries et al., *Heterocycles*, 23 (8), 1915 (1985); BE 900 718 A (Sandoz) and Japanese Patent Pub. No. 6-0163-882-A (Sanruku Ocean).

In preferred compounds of Formula I, $R^1$ is hydrogen. More preferably, $R^1$ is hydrogen and $R^2$ is (R)—$CH_3CH(OH)$— or (R)—$CH_3CH(F)$—. In the most preferred case, $R^1$ is hydrogen and $R^2$ is (R)—$CH_3CH(OH)$—. While R=H is usually preferred, there are instances in which R=$CH_3$ may provide improved chemical stability, water solubility, or pharmacokinetic behavior. The substituent R=$CH_3$ may be of either configuration, i.e., the $\alpha$ or $\beta$-stereoisomer. Additionally, in preferred compounds, at least one $R^a$ in the 4-, 6-, 7-, or 8-position of the phenanthridine is other than hydrogen if Y is substituent b), at least one $R^a$ in the 3-, 4-, 6- or 7-position of the phenanthridine is other than hydrogen if Y is substituent a), at least one $R^a$ in the 1-, 6-, 7-, or 8-position of the phenanthridine is other than hydrogen if Y is substituent d), or at least one $R^a$ in the 3-, 4-, 6- or 10-position of the phenanthridine is other than hydrogen if Y is substituent c). In the most preferred compounds, in total, up to two $R^a$ substituents in two of those positions are other than hydrogen.

Suitable $R^a$ are described above in the text associated with Formula I. Among preferred $R^a$ are $C_{1-4}$ alkyl mono-substituted with hydroxy, such as, —COOMe; carbamoyl, such as, —$CONH_2$; hydroxoximinomethyl, such as, —CH=NOH or cyano.

For example, when Y is substituent b), in regard to this preferred substitution, the hydroxymethyl groups may be obtained in the 4, 7, and 8-positions of the phenanthridine as follows. Thus referring to Flow Sheet B, methyl, as a precursor substituent, is substituted on starting materials B-3 and/or B-5 in the appropriate positions by well know means. Subsequently the methyl substituent of methyl-substituted B-3, B-5, B-6 or B-8 may be oxidized e.g. to carboxy with ruthenium tetroxide or to bromomethyl with N-bromosuccinimide. The resultant carboxy or bromomethyl substituted starting material may be further elaborated. In the case of the bromomethyl substituent, conversion to a hydroxymethyl substituted precursor may be accomplished by a three-step sequence. Reaction of the bromomethyl compound with potassium acetate in DMF at 80° C. gives the corresponding acetoxymethyl compound. Removal of the acetate group, e.g. by hydrolysis with methanolic sodium hydroxide or by reduction with diisobutylaluminium hydride in THF, gives the hydroxymethyl substituted compound which may then be incorporated in the synthesis of a correspondingly substituted B10. When necessary the hydroxymethyl moiety may be protected by silylation with t-butyldimethylsilyl chloride, triethylamine and 4-dimethylaminopyridine in dichloromethane. Further elaboration of B-3, B-5, B-6, B-8 or B-10 provides other moieties as described hereinbelow.

The preferred formyl substitution on the phenanthridine may be obtained from the hydroxymethyl substituted starting material just described by a Swern oxidation. For example, the hydroxymethyl is oxidized in methylene chloride at from −70° C. to room temperature employing oxalyl chloride-dimethyl sulfoxide followed by triethylamine as the active agent. Obviously, the position of the resultant formyl substitution will depend upon the position of the hydroxymethyl substitution on compound B-1, B-5 B-6, B-8or B-10.

The preferred —CH=NOH substitution on the phenanthridine may be conveniently obtained from the formyl substitution just described. This is accomplished simply by exposing the formyl substituted compound to hydroxylamine in an appropriate solvent at room temperature.

The preferred cyano substitution on the phenanthridine may be obtained from the —CH=NOH substitution just described. The —CH=NOH substituted compound is dehydrated with triflic anhydride and triethylamine in a solvent at −70° C.

The preferred alkoxycarbonyl substitution on the phenanthridine may be obtained from the hydroxymethyl substituted starting material. For example, the substituted compound B-7 or B-8 is oxidized with Jones reagent to convert the hydroxymethyl substituent to a carboxylic acid group. Such a group may then be esterified by a procedure well known in the art, such as by treatment with diazomethane.

The preferred carbamoyl substitution on the phenanthridine, may be obtained by oxidizing the hydroxymethyl group with Jones reagent to the corresponding carboxylic acid group as described above. This carboxylic acid substituent is converted to the carboxamide group, —$CONH_2$, by sequentially contacting with 1-ethyl-3-(3-dimethylaminopropyl)carbodiimide hydrochloride, 1-hydroxybenzotriazole, and ammonia in an organic solvent at room temperature, Substituted amides may of course be obtained by replacing ammonia with the corresponding substituted amine.

In the preparation methods described above, the carboxyl group at the B-position and the hydroxyl group at the 8-position of the carbapenem remain blocked by protecting groups until the penultimate product is prepared. Deblocking may be carried out in a conventional manner. For compounds prepared via Flow Sheet F, if the hydroxyethyl moiety has been protected deprotection is conducted sequentially. Thus, compound F-3 where $R^P$ is a trialkylsilyl is exposed initially to aqueous acidic conditions, acetic acid or dilute HCl or the like, in an organic solvent such as tetrahydrofuran at 0° C. to ambient temperature for from a few minutes to several hours. The unsilylated carbapenem may be isolated by conventional techniques, but is more conveniently taken into the final deprotection process. Thus, addition of a base such as $NaHCO_3$ or $KHCO_3$, and optionally a buffer such as MOPS buffer, phosphate buffer and the like, and a suitable catalyst, such as 5%–10% Pd/C, 5%–10% $Rh/Al_2O_3$, 5%–10% Rh/C and the like, followed by hydrogenation provides for the removal of the p-nitrobenzyl protecting group and the formation of the final compound of Formula I.

With reference to the above definitions, "alkyl" means a straight or branched chain aliphatic hydrocarbon radical.

The term "heteroatom" means N, S, or O, selected on an independent basis.

The term "heteroaryl" has been defined herein, in relation to the $R^x$ group, to have a specific and limited meaning, being only monocyclic. It is required that the monocyclic heteroaryl have at least one nitrogen atom, and optionally at most only one additional oxygen or sulfur heteroatom may be present. Heteroaryls of this type are pyrrole and pyridine (1N); and oxazole, thiazole or oxazine (1N +1 O or 1 S). While additional nitrogen atoms may be present together with the first nitrogen and oxygen or sulfur, giving, e.g., a thiadiazole (2N's+1S), the preferred heteroaryls are those where only nitrogen heteroatoms are present when there is more 5 than one. Typical of these are pyrazole, imidazole, pyrimidine and pyrazine (2 N's) and triazine (3 N's).

The heteroaryl group of $R^x$ is always optionally mono-substituted by $R^q$, defined above, and substitution can be on one of the carbon atoms or one of the heteroatoms, although in the latter case certain substitutent choices may not be appropriate.

Listed in Tables I and II are specific compounds of the instant invention. The attachment point (art pt) represents the position on the phenanthridine ring where the carbapenem nucleus is attached. When the substituent $R^{a'}$ (which is $R^a$ when it is not hydrogen) is not present in a position on the phenanthridinyl moiety it is understood that the substituent at that position is hydrogen. These compounds are meant to be illustrative and are not limiting.

TABLE I

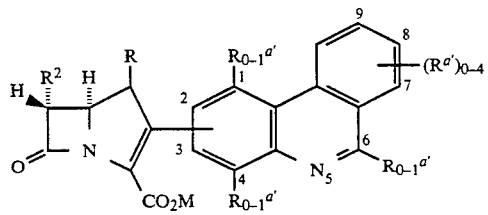

| Att pt | R | $R^2$ | M | $R^{a'}$ | $R^{a'}$ position |
|---|---|---|---|---|---|
| 2 | —H | (R)—CH(OH)CH₃ | —Na⁺ | —OCH₃ | 4,7 |
| 3 | —H | (R)—CH(OH)CH₃ | —Na⁺ | —OCH₂CO₂Me | 4 |
| 3 | —H | (R)—CH(OH)CH₃ | —H | —OCH₂CH₂OH | 8 |
| 2 | —H | (R)—CH(OH)CH₃ | —Na⁺ | —CF₃ | 7 |
| 2 | —H | (R)—CH(OH)CH₃ | —Na⁺ | —F | 7 |
| 3 | —H | (R)—CH(OH)CH₃ | —Na⁺ | —Cl | 8 |
| 3 | —H | (R)—CH(OH)CH₃ | —Na⁺ | —Br | 7 |
| 2 | —H | (R)—CH(OH)CH₃ | —Na⁺ | —F | 4,7,8 |
| 2 | —H | (R)—CH(OH)CH₃ | —Na⁺ | —OH | 7,8 |
| 3 | —CH₃ | (R)—CH(OH)CH₃ | —H | —OCOCH₃ | 8 |
| 2 | —H | (R)—CH(OH)CH₃ | —Na⁺ | —OCONH₂ | 8 |
| 2 | —H | (R)—CH(OH)CH₃ | —Na⁺ | —SCH₃ | 4 |
| 2 | —H | (R)—CH(F)CH₃ | —Na⁺ | —SOCH₃ | 4 |
| 3 | —H | (R)—CH(OH)CH₃ | —Na⁺ | —SO₂CH₃ | 8 |
| 3 | —H | (R)—CH(OH)CH₃ | —Na⁺ | —SCH₂CH₂OH | 8 |
| 2 | —H | (R)—CH(OH)CH₃ | —Na⁺ | —SOCH₂CH₂OH | 7 |
| 2 | —H | (R)—CH(OH)CH₃ | —Na⁺ | —SCH₂CONH₂ | 7 |
| 3 | —H | (R)—CH(OH)CH₃ | —Na⁺ | —SO₂NH₂ | 8 |
| 2 | —H | (R)—CH(OH)CH₃ | —Na⁺ | —SO₂N(CH₃)₂ | 7,8 |
| 2 | —H | —CF₂CH₃ | —Na⁺ | —NHCHO | 7,8 |
| 3 | —H | (R)—CH(OH)CH₃ | —Na⁺ | —NHCOCH₃ | 6 |
| 3 | —H | (R)—CH(OH)CH₃ | —H | —NHCO₂CH₃ | 10 |
| 3 | —H | (R)—CH(OH)CH₃ | —Na⁺ | —NHSO₂CH₃ | 7 |
| 2 | —H | (R)—CH(F)CH₃ | —Na⁺ | —CN | 6 |
| 3 | —H | (R)—CH(F)CH₃ | —Na⁺ | —CHO | 9 |
| 2 | —H | (R)—CH(OH)CH₃ | —Na⁺ | —COCH₃ | 10 |
| 2 | —H | (R)—CH(OH)CH₃ | —Na⁺ | —COCH₂OH | 8 |
| 3 | —CH₃ | (R)—CH(OH)CH₃ | —Na⁺ | —CH=NOH | 8 |
| 3 | —H | (R)—CH(OH)CH₃ | —Na⁺ | —CH=NOCH₃ | 7 |
| 3 | —CH₃ | (R)—CH(OH)CH₃ | —H | —CH=NOCH₂CO₂Me | 9 |
| 2 | —H | (R)—CH(OH)CH₃ | —Na⁺ | —CH=NOCMe₂CO₂Me | 6 |

TABLE I-continued

| Att pt | R | $R^2$ | M | $R^{a'}$ | $R^{a'}$ position |
|---|---|---|---|---|---|
| 2 | —H | (R)—CH(OH)CH$_3$ | —Na$^+$ | —CH=NOCMe$_2$CO$_2$Me | 8 |
| 2 | —H | (R)—CH(OH)CH$_3$ | —Na$^+$ | —CO$_2$CH$_2$CH$_2$OH | 7 |
| 3 | —H | (R)—CH(F)CH$_3$ | —Na$^+$ | —CONH$_2$ | 7,8 |
| 3 | —H | (R)—CH(OH)CH$_3$ | —Na$^+$ | —CONHCH$_3$ | 9 |
| 3 | —H | (R)—CH(OH)CH$_3$ | —Na$^+$ | —CON(CH$_3$)$_2$ | 8 |
| 2 | —H | (R)—CH(OH)CH$_3$ | —K$^+$ | —CONHCH$_2$CN | 4 |
| 2 | —H | (R)—CH(OH)CH$_3$ | —K$^+$ | —CONHCH$_2$CONH$_2$ | 8 |
| 3 | —H | (R)—CH(OH)CH$_3$ | —K$^+$ | —CONHCH$_2$CO$_2$Me | 7 |
| 2 | —H | (R)—CH(OH)CH$_3$ | —Na$^+$ | —CONHOH | 9 |
| 3 | —H | (R)—CH(OH)CH$_3$ | —Na$^+$ | —CONHOCH$_3$ | 7 |
| 2 | —H | (R)—CH(OH)CH$_3$ | —Na$^+$ | -teterazolyl | 8 |
| 3 | —H | (R)—CH(OH)CH$_3$ | —Na$^+$ | —CO$_2$Me | 7 |
| 2 | —H | (R)—CH(OH)CH$_3$ | —Na$^+$ | —SCF$_3$ | 4 |
| 2 | —H | (R)—CH(OH)CH$_3$ | —H | —PO$_3$MeH | 8 |
| 2 | —H | (R)—CH(OH)CH$_3$ | —Na$^+$ | —CONHSO$_2$Ph | 10 |
| 2 | —H | (R)—CH(OH)CH$_3$ | —Na$^+$ | —CONHSO$_2$NH$_2$ | 7 |
| 3 | —H | (R)—CH(OH)CH$_3$ | —K$^+$ | —SO$_3$Me | 8 |
| 3 | —H | (R)—CH(OH)CH$_3$ | —Na$^+$ | —SO$_2$NHCN | 8 |
| 2 | —H | (R)—CH(F)CH$_3$ | —Na$^+$ | —SO$_2$NHCONH$_2$ | 7 |
| 2 | —H | (R)—CH(OH)CH$_3$ | —Na$^+$ | —CH=CHCN | 7 |
| 2 | —H | (R)—CH(OH)CH$_3$ | —Na$^+$ | —CH=CHCONH$_2$ | 8 |
| 3 | —H | (R)—CH(OH)CH$_3$ | —Na$^+$ | —CH=CHCO$_2$Me | 9 |
| 3 | —H | (R)—CH(OH)CH$_3$ | —Na$^+$ | —C≡C—CONH$_2$ | 8 |
| 3 | —CH$_3$ | (R)—CH(OH)CH$_3$ | —Na$^+$ | —C≡C—CN | 7 |
| 3 | —H | (R)—CH(OH)CH$_3$ | —K$^+$ | —CH$_2$OH | 6 |
| 2 | —H | (R)—CH(OH)CH$_3$ | —K$^+$ | —CH$_2$N$_3$ | 7 |
| 3 | —H | (R)—CH(OH)CH$_3$ | —Na$^+$ | —CH$_2$CO$_2$Me | 7 |
| 2 | H | (R)—CH(OH)CH$_3$ | —Na$^+$ | —CN | 4 |
| 2 | H | (R)—CH(OH)CH$_3$ | —Na$^+$ | —CN | 7 |
| 3 | H | (R)—CH(OH)CH$_3$ | —Na$^+$ | —CN | 8 |
| 3 | H | (R)—CH(OH)CH$_3$ | —Na$^+$ | —CN | 9 |
| 3 | H | (R)—CH(OH)CH$_3$ | —Na$^+$ | —CN | 10 |
| 2 | H | (R)—CH(OH)CH$_3$ | —Na$^+$ | —CHO | 4 |
| 3 | H | (R)—CH(OH)CH$_3$ | —Na$^+$ | —CHO | 6 |
| 2 | H | (R)—CH(OH)CH$_3$ | —Na$^+$ | —CHO | 7 |
| 3 | H | (R)—CH(OH)CH$_3$ | —Na$^+$ | —CHO | 8 |
| 2 | H | (R)—CH(OH)CH$_3$ | —Na$^+$ | —CHO | 9 |
| 2 | H | (R)—CH(OH)CH$_3$ | —Na$^+$ | —CHO | 10 |
| 2 | H | (R)—CH(OH)CH$_3$ | —Na$^+$ | —CONH$_2$ | 4 |
| 3 | H | (R)—CH(OH)CH$_3$ | —Na$^+$ | —CONH$_2$ | 7 |
| 3 | H | (R)—CH(OH)CH$_3$ | —Na$^+$ | —CONH$_2$ | 8 |
| 2 | H | (R)—CH(OH)CH$_3$ | —Na$^+$ | —CONH$_2$ | 9 |
| 3 | H | (R)—CH(OH)CH$_3$ | —Na$^+$ | —CONH$_2$ | 10 |
| 2 | H | (R)—CH(OH)CH$_3$ | —Na$^+$ | —CH=NOH | 4 |
| 2 | H | (R)—CH(OH)CH$_3$ | —Na$^+$ | —CH=NOH | 7 |
| 2 | H | (R)—CH(OH)CH$_3$ | —Na$^+$ | —CH=NOH | 8 |
| 2 | H | (R)—CH(OH)CH$_3$ | —Na$^+$ | —CH=NOH | 9 |
| 3 | H | (R)—CH(OH)CH$_3$ | —Na$^+$ | —CH=NOH | 10 |
| 3 | H | (R)—CH(OH)CH$_3$ | —Na$^+$ | —CH$_2$OH | 7 |
| 3 | H | (R)—CH(OH)CH$_3$ | —Na$^+$ | —CH$_2$OH | 9 |
| 3 | H | (R)—CH(OH)CH$_3$ | —Na$^+$ | — | — |

TABLE II

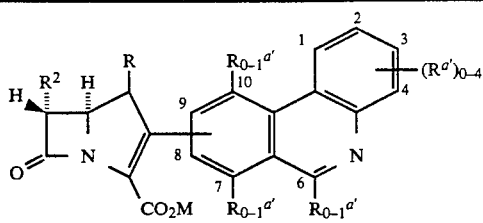

| Att pt | R | R² | M | Rᵃ' | Rᵃ' position |
|---|---|---|---|---|---|
| 9 | —H | (R)—CH(OH)CH₃ | —Na⁺ | —OCH₃ | 7,3 |
| 8 | —H | (R)—CH(OH)CH₃ | —Na⁺ | —OCH₂CO₂Me | 10 |
| 8 | —H | (R)—CH(OH)CH₃ | —H | —OCH₂CH₂OH | 3 |
| 9 | —H | (R)—CH(OH)CH₃ | —K⁺ | —CF₃ | 4 |
| 9 | —H | (R)—CH(OH)CH₃ | —Na⁺ | —F | 3 |
| 8 | —H | (R)—CH(OH)CH₃ | —Na⁺ | —Cl | 3 |
| 8 | —H | (R)—CH(OH)CH₃ | —Na⁺ | —Br | 4 |
| 9 | —H | (R)—CH(OH)CH₃ | —K⁺ | —F | 7,4,3 |
| 8 | —H | (R)—CH(OH)CH₃ | —Na⁺ | —OH | 3,4 |
| 8 | —CH₃ | (R)—CH(OH)CH₃ | —H | —OCOCH₃ | 4 |
| 9 | —H | (R)—CH(OH)CH₃ | —Na⁺ | —OCONH₂ | 4 |
| 9 | —H | (R)—CH(OH)CH₃ | —Na⁺ | —SCH₃ | 7 |
| 9 | —H | (R)—CH(F)CH₃ | —Na⁺ | —SOCH₃ | 7 |
| 8 | —H | (R)—CH(OH)CH₃ | —K⁺ | —SO₂CH₃ | 3 |
| 8 | —H | (R)—CH(OH)CH₃ | —Na⁺ | —SCH₂CH₂OH | 3 |
| 9 | —H | (R)—CH(OH)CH₃ | —Na⁺ | —SOCH₂CH₂OH | 4 |
| 9 | —H | (R)—CH(OH)CH₃ | —Na⁺ | —SCH₂CONH₂ | 3 |
| 8 | —H | (R)—CH(OH)CH₃ | —Na⁺ | —SO₂NH₂ | 3 |
| 9 | —H | (R)—CH(OH)CH₃ | —Na⁺ | —SO₂N(CH₃)₂ | 4,3 |
| 9 | —H | —CF₂CH₃ | —K⁺ | —NHCHO | 4,3 |
| 8 | —H | (R)—CH(OH)CH₃ | —Na⁺ | —NHCOCH₃ | 6 |
| 8 | —H | (R)—CH(OH)CH₃ | —H | —NHCO₂CH₃ | 3 |
| 8 | —H | (R)—CH(OH)CH₃ | —Na⁺ | —NHSO₂CH₃ | 4 |
| 9 | —H | (R)—CH(F)CH₃ | —Na⁺ | —CN | 6 |
| 8 | —H | (R)—CH(F)CH₃ | —K⁺ | —CHO | 3 |
| 9 | —H | (R)—CH(OH)CH₃ | —K⁺ | —COCH₃ | 4 |
| 9 | —H | (R)—CH(OH)CH₃ | —Na⁺ | —COCH₂OH | 3 |
| 8 | —CH₃ | (R)—CH(OH)CH₃ | —Na⁺ | —CH=NOH | 3 |
| 8 | —H | (R)—CH(OH)CH₃ | —Na⁺ | —CH=NOCH₃ | 3 |
| 8 | —CH₃ | (R)—CH(OH)CH₃ | —H | —CH=NOCH₂CO₂Me | 3 |
| 8 | —H | (R)—CH(OH)CH₃ | —Na⁺ | —CH=NOCMe₂CO₂Me | 6 |
| 9 | —H | (R)—CH(OH)CH₃ | —Na⁺ | —CH=NOCMe₂CO₂Me | 3 |
| 8 | —H | (R)—CH(OH)CH₃ | —K⁺ | —CO₂CH₂CH₂OH | 4 |
| 8 | —H | (R)—CH(F)CH₃ | —Na⁺ | —CONH₂ | 3,2 |
| 8 | —H | (R)—CH(OH)CH₃ | —Na⁺ | —CONHCH₃ | 2 |
| 9 | —H | (R)—CH(OH)CH₃ | —Na⁺ | —CON(CH₃)₂ | 1 |
| 9 | —H | (R)—CH(OH)CH₃ | —Na⁺ | —CONHCH₂CN | 7 |
| 8 | —H | (R)—CH(OH)CH₃ | —Na⁺ | —CONHCH₂CONH₂ | 3 |
| 8 | —H | (R)—CH(OH)CH₃ | —Na⁺ | —CONHCH₂CO₂Me | 4 |
| 9 | —H | (R)—CH(OH)CH₃ | —Na⁺ | —CONHOH | 2 |
| 9 | —H | (R)—CH(OH)CH₃ | —Na⁺ | —CONHOCH₃ | 2 |
| 8 | —H | (R)—CH(OH)CH₃ | —Na⁺ | -teterazolyl | 3 |
| 9 | —H | (R)—CH(OH)CH₃ | —Na⁺ | —CO₂Me | 3 |
| 9 | —H | (R)—CH(OH)CH₃ | —Na⁺ | —SCF₃ | 7 |
| 8 | —H | (R)—CH(OH)CH₃ | —H | —PO₃MeH | 3 |
| 8 | —H | (R)—CH(OH)CH₃ | —Na⁺ | —CONHSO₂Ph | 1 |
| 8 | —H | (R)—CH(OH)CH₃ | —Na⁺ | —CONHSO₂NH₂ | 4 |
| 9 | —H | (R)—CH(OH)CH₃ | —K⁺ | —SO₃Me | 3 |
| 9 | —H | (R)—CH(OH)CH₃ | —Na⁺ | —SO₂NHCN | 3 |
| 8 | —H | (R)—CH(F)CH₃ | —Na⁺ | —SO₂NHCONH₂ | 3 |
| 9 | —H | (R)—CH(OH)CH₃ | —Na⁺ | —CH=CHCN | 3 |
| 8 | —H | (R)—CH(OH)CH₃ | —Na⁺ | —CH=CHCONH₂ | 3 |
| 8 | —H | (R)—CH(OH)CH₃ | —Na⁺ | —CH=CHCO₂Me | 3 |
| 9 | —H | (R)—CH(OH)CH₃ | —Na⁺ | —C≡C—CONH₂ | 3 |
| 9 | —CH₃ | (R)—CH(OH)CH₃ | —Na⁺ | —C≡C—CN | 4 |
| 9 | —H | (R)—CH(OH)CH₃ | —K⁺ | —CH₂OH | 6 |
| 8 | —H | (R)—CH(OH)CH₃ | —Na⁺ | —CH₂N₃ | 3 |
| 8 | —H | (R)—CH(OH)CH₃ | —Na⁺ | —CH₂CO₂Me | 3 |
| 9 | H | (R)—CH(OH)CH₃ | —Na⁺ | —CN | 7 |
| 8 | H | (R)—CH(OH)CH₃ | —Na⁺ | —CN | 4 |
| 8 | H | (R)—CH(OH)CH₃ | —Na⁺ | —CN | 3 |
| 9 | H | (R)—CH(OH)CH₃ | —Na⁺ | —CN | 2 |
| 9 | H | (R)—CH(OH)CH₃ | —Na⁺ | —CN | 1 |
| 9 | H | (R)—CH(OH)CH₃ | —Na⁺ | —CHO | 7 |
| 8 | H | (R)—CH(OH)CH₃ | —Na⁺ | —CHO | 6 |
| 8 | H | (R)—CH(OH)CH₃ | —Na⁺ | —CHO | 4 |
| 8 | H | (R)—CH(OH)CH₃ | —Na⁺ | —CHO | 3 |
| 9 | H | (R)—CH(OH)CH₃ | —Na⁺ | —CHO | 2 |
| 8 | H | (R)—CH(OH)CH₃ | —Na⁺ | —CHO | 1 |

TABLE II-continued

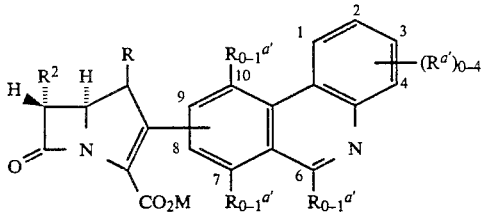

| Att pt | R | $R^2$ | M | $R^{a'}$ | $R^{a'}$ position |
|---|---|---|---|---|---|
| 9 | H | (R)—CH(OH)CH$_3$ | —Na$^+$ | —CONH$_2$ | 7 |
| 8 | H | (R)—CH(OH)CH$_3$ | —Na$^+$ | —CONH$_2$ | 4 |
| 8 | H | (R)—CH(OH)CH$_3$ | —Na$^+$ | —CONH$_2$ | 3 |
| 8 | H | (R)—CH(OH)CH$_3$ | —Na$^+$ | —CONH$_2$ | 2 |
| 8 | H | (R)—CH(OH)CH$_3$ | —Na$^+$ | —CONH$_2$ | 1 |
| 9 | H | (R)—CH(OH)CH$_3$ | —Na$^+$ | —CH=NOH | 7 |
| 8 | H | (R)—CH(OH)CH$_3$ | —Na$^+$ | —CH=NOH | 4 |
| 8 | H | (R)—CH(OH)CH$_3$ | —Na$^+$ | —CH=NOH | 3 |
| 8 | H | (R)—CH(OH)CH$_3$ | —Na$^+$ | —CH=NOH | 2 |
| 9 | H | (R)—CH(OH)CH$_3$ | —Na$^+$ | —CH=NOH | 1 |
| 9 | H | (R)—CH(OH)CH$_3$ | —Na$^+$ | —CH$_2$OH | 4 |
| 9 | H | (R)—CH(OH)CH$_3$ | —K$^+$ | —CH$_2$OH | 2 |
| 8 | H | (R)—CH(OH)CH$_3$ | —Na$^+$ | — | — |

The carbapenem compounds of the present invention are useful per se and in their pharmaceutically acceptable salt and ester forms in the treatment of bacterial infections in animal and human subjects, The term "pharmaceutically acceptable ester or salt" refers to those salt and ester forms of the compounds of the present invention which would be apparent to the pharmaceutical chemist, i.e., those which are non-toxic and which would favorably affect the pharmacokinetic properties of said compounds, their palatability, absorption, distribution, metabolism and excretion. Other factors, more practical in nature, which are also important in the selection, are cost of the raw materials, ease of crystallization, yield, stability, hygroscopicity, and flowability of the resulting bulk drug. Conveniently, pharmaceutical compositions may be prepared from the active ingredients in combination with pharmaceutically acceptable carriers. Thus, the present invention is also concerned with pharmaceutical compositions and methods of treating bacterial infections utilizing as an active ingredient the novel carbapenem compounds of the present invention.

The pharmaceutically acceptable salts referred to above may take the form —COOM. The M may be an alkali metal cation such as sodium or potassium. Other pharmaceutically acceptable cations for M may be calcium, magnesium, zinc, ammonium, or alkylammonium cations such as tetramethylammonium, tetrabutylammonium, choline, triethylhydroammonium, meglumine, triethanolhydroammonium, etc.

The pharmaceutical acceptable esters of the novel carbapenem compounds of the present invention are such as would be readily apparent to a medicinal chemist, and include, for example, those described in detail in U.S. Pat. No. 4,309,438, Column 9, line 61 to Column 12, line 51, which is incorporated herein by reference. Included within such pharmaceutically acceptable esters are those which are hydrolyzed under physiological conditions, such as pivaloyloxymethyl, acetoxymethyl, phthalidyl, indanyl and methoxymethyl, and those described in detail in U.S. Pat. No. 4,479,947, which is incorporated herein by reference.

The novel carbapenem compounds of the present invention may take the form COOM, where M is a readily removable carboxyl protecting group. Such conventional blocking groups consist of known ester groups which are used to protectively block the carboxyl group during the synthesis procedures described above. These conventional blocking groups are readily removable, i.e., they can be removed, if desired, by procedures which will not cause cleavage or other disruption of the remaining portions of the molecule. Such procedures include chemical and enzymatic hydrolysis, treatment with chemical reducing or oxidizing agents under mild conditions, treatment with a transition metal catalyst and a nucleophile, and catalytic hydrogenation. Examples of such ester protecting groups include benzhydryl, p-nitrobenzyl, 2-naphthylmethyl, allyl, benzyl, t-butyl, trichloroethyl, silyl such as trimethylsilyl, trimethylsilylethyl, phenacyl, p-methoxybenzyl, acetonyl, o-nitrobenzyl, p-methoxyphenyl and 4-pyridylmethyl.

The compounds of the present invention are valuable antibacterial agents active against various Gram-positive and to a lesser extent Gram-negative bacteria and accordingly find utility in human and veterinary medicine. The antibacterials of the invention are not limited to utility as medicaments; they may be used in all manner of industry, for example: additives to animal feed, preservation of food, disinfectants, and in other industrial systems where control of bacterial growth is desired. For example, they may be employed in aqueous compositions in concentrations ranging from 0.1 to 100 parts of antibiotic per million parts of solution in order to destroy,or inhibit the growth of harmful bacteria on medical and dental equipment and as bactericides in industrial applications, for example in waterbased paints and in the white water of paper mills to inhibit the growth of harmful bacteria.

The compounds of this invention may be used in any of a variety of pharmaceutical preparations. They may be employed in capsule, powder form, in liquid solution, or in suspension. They may be administered by a variety of means; those of principal interest include: topically or parenterally by injection (intravenously or intramuscularly).

Compositions for injection, a preferred route of delivery, may be prepared in unit dosage form in ampules, or in multidose containers. The compositions may take such forms as suspensions, solutions, or emulsions in oily or aqueous vehicles, and may contain formulatory agents. Alternatively, the active ingredient may be in powder form for reconstitution, at the time of delivery, with a suitable vehicle, such as sterile water. Topical applications may be formulated in hydrophobic or hydrophilic bases as ointments, creams, lotions, paints, or powders.

The dosage to be administered depends to a large extent upon the condition and size of the subject being treated as well as the route and frequency of administration, the parenteral route by injection being preferred for generalized infections. Such matters, however, are left to the routine discretion of the therapist according to principles of treatment well known in the anti-bacterial art. Another factor influencing the precise dosage regimen, apart from the nature of the infection and peculiar identity of the individual being treated, is the molecular weight of the chosen species of this invention.

The compositions for human delivery per unit dosage, whether liquid or solid, may contain from 0.1% to 99% of active material, the preferred range being from about 10–60%. The composition will generally contain from about 15 mg to about 1500 mg of the active ingredient; however, in general, it is preferable to employ a dosage amount in the range of from about 250 mg to 1000 mg. In parenteral administration, the unit dosage is usually the pure compound I in sterile water solution or in the form of a soluble powder intended for solution.

The preferred method of administration of the Formula I antibacterial compounds is parenteral by i.v. infusion, i.v. bolus, or i.m. injection.

For adults, 5–50 mg of Formula I antibacterial compounds per kg of body weight given 2, 3, or 4 times per day is preferred. Preferred dosage is 250 mg to 1000 mg of the Formula I antibacterial given two (b.i.d.) three (t.i.d.) or four (q.i.d.) times per day. More specifically, for mild infections a dose of 250 mg t.i.d. or q.i.d. is recommended. For moderate infections against highly susceptible gram positive organisms a dose of 500 mg t.i.d. or q.i.d. is recommended. For severe, life-threatening infections against organisms at the upper limits of sensitivity to the antibiotic, a dose of 1000 mg t.i.d. or q.i.d. is recommended.

For children, a dose of 5–25 mg/kg of body weight given 2, 3, or 4 times per day is preferred; a dose of 10 mg/kg t.i.d. or q.i.d. is usually recommended.

Antibacterial compounds of Formula I are of the broad class known as carbapenems or 1-carbadethiapenems. Naturally occuring carbapenems are susceptible to attack by a renal enzyme known as dehydropeptidase (DHP). This attack or degradation may reduce the efficacy of the carbapenem antibacterial agent. The compounds of the present invention, on the other hand, are significantly less subject to such attack, and therefore may not require the use of a DHP inhibitor. However, such use is optional and contemplated to be part of the present invention. Inhibitors of DHP and their use with carbapenem antibacterial agents are disclosed in the prior art [see European Patent Applications No. 79102616.4 filed Jul. 24, 1979 (Patent No. 0 007 614); and No. 82107174.3, filed Aug. 9, 1982 (Publication No. 0 072 014)].

The compounds of the present invention may, where DHP inhibition is desired or necessary, be combined or used with the appropriate DHP inhibitor as described in the aforesaid patents and published application. Thus, to the extent that the cited European patent applications 1.) define the procedure for determining DHP susceptibility of the present carbapenems and 2.) disclose suitable inhibitors, combination compositions and methods of treatment, they are incorporated herein by reference. A preferred weight ratio of Formula I compound: DHP inhibitor in the combination compositions is about 1:1. A preferred DHP inhibitor is 7-(L-2-amino-2-carboxyethylthio)-2-(2,2-dimethylcyclopropanecarboxamide)-2-heptenoic acid or a useful salt thereof.

The invention is further defined by reference to the following examples, which are illustrative and not limiting. All temperatures are in degrees Celsius.

EXAMPLE 1

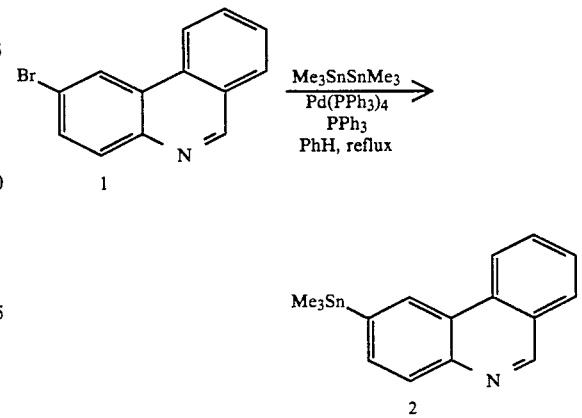

Dry nitrogen gas was bubbled through a mixture of 1 (300 mg; 1.16 mmol), hexamethylditin (418 mg; 1.28 mmol; 1.1 equiv.), Pd(PPh₃)₄ (67 mg; 0.058 mmol; 5 mol %) and triphenylphosphine (9 mg; 0.035 mmol; 3 mol %) in toluene (6 mL) for 15 minutes. The reaction mixture was then heated to reflux for 1 hr. 45 min. before being poured into Et₂O. The organic layers were washed with H₂O (1X), saturated NaHCO₃ (3X), H₂O (1X) and brine (1X). The reaction mixture was dried over MgSO₄, filtered and the solvent was removed in vacuo. Purification via SiO₂ flash column chromatography (20% EtOAc/hexanes) provided the stannane 2.

$^1$H NMR (200 MHz, CDCl₃)δ0.42 (s, 9H), 7.68–7.75 (m 1H), 7.85–7.92 (m, 2H), 8.06 (d, J=7.8 Hz, 1H), 8.17 (d, J=7.9 Hz, 1H), 8.67–8.74 (m, 2H), 9.28 (s, 1H),

EXAMPLE 2

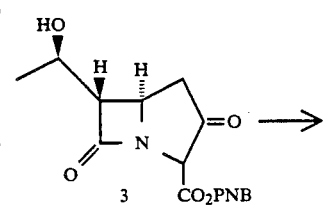

-continued

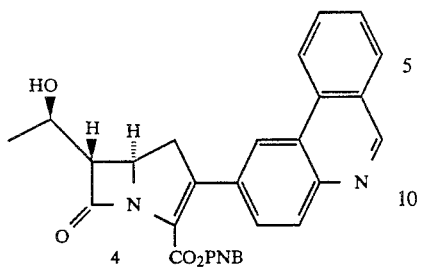

To a stirred solution of the bicyclic β-keto ester 3 (131.3 mg, 0.377 mmol) in dry THF (1.9 mL) at −78° C. under $N_2$ was added diisopropylamine (58.2 μL, 0.415 mmol, 1.2 eq). The resultant yellow mixture was stirred for 10 minutes before trifluoromethanesulfonic anhydride (69.8 μL, 0.415 mmol, 1.2 eq) was added. After 15 minutes the reaction mixture was treated sequentially with anhydrous N-methyl-2-pyrrolidinone (1.9 mL), the $Pd_2(dba)_3 \cdot CHCl_3$ catalyst (7.8 mg, $7.55 \times 10^{-3}$ mmol, 2.0 mol %), the aryl-stannane % prepared as described in Example 1 (117.2 mg, 0.343 mmol), and diisopropylammoniumchloride (47.2 mg; 0.34 mmol; 1.0 eq). The low temperature bath was then removed and the reaction vessel was placed in a warm water bath to quickly reach ambient temperature. The solution was stired for 2 days at ambient temperature.

The reaction was then poured into ether containing some ethyl acetate and washed with water (3×) and brine. The organic layer was dried ($MgSO_4$), filtered, and evaporated in vacuo. Purification using flash chromatography (10% MeOH/EtOAc) provided the coupled product 4. $^1H$ NMR (400 MHz, $d_6$-DMSO)δ1.19 (d, J=6.3 Hz, 3H), 3.32(½ ABX, obscured by $H_2O$ peak in DMSO, 1H), 3.48 (dd, J=6.1, 3.0 Hz, 1H), 3.73 (½ ABX, $J_{AB}$=18.9 Hz, $J_{AX}$=8.7 Hz, 1H), 3.90–4.06 (m, 1H), 4.31 (dt, J=8.8, 2.8 Hz, 1H), 5.25 (ABq, $J_{AB}$=14.9 Hz, $\Delta v_{AB}$=42.8 Hz, 2H), 7.32 ( d, J=8.3 Hz, 2H), 7.72–7.82 (m, 2H), 7.90(t, J=7.1 Hz, 1H), 8.00 (d, J=8.5 Hz, 1H), 8.19 (d, J=8.01 Hz, 1H), 8.71 (d, J=8.4 Hz, 1H ), 8.76 ( s, 1H), 9.33 (s, 1H); I.R. (KBr) 1775, 1720, 1600, 1520 $cm^{-1}$.

EXAMPLE 3

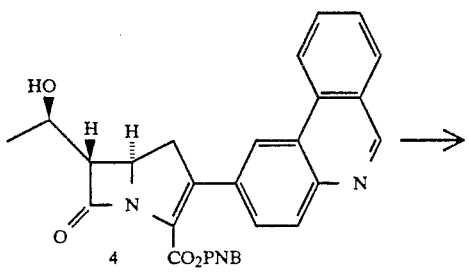

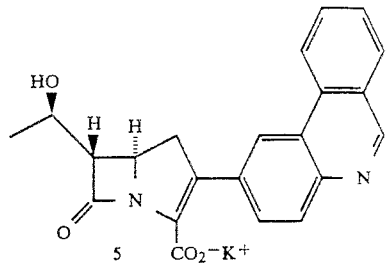

Potassium (5R,6S)-2-(2-phenanthridinyl)-6-(1R-hydroxyethyl)carbapen-2-em-3-carboxylate To a stirred solution of 4 (25 mg, 0.0503 mmol) and potassium bicarbonate (6.4 mg, 0.0636 mmol, 1.2 eq) in 2:1 $THF/H_2O$ (10 mL) was added 10% Pd/C catalyst (2.5 mg, 10% wt), and the reaction mixture was hydrogenated under an $H_2$ balloon at ambient temperature for 50 minutes. The mixture was then filtered through a pad of celite using water as the eluant, and the THF solvent from the filtrate was removed in vacuo. The remaining water was then frozen and lyophilized at 0° C. Crude 27 was redissolved in a minimal amount of $H_2O/CH_3CN$ and purified using Analtech reverse phase prep-plates (4:1 $H_2O/CH_3CN$) to provide compound 5. $^1H$ NMR (400 MHz, (2:1) $D_2O/CD_3CN$)δ1.69 (d, J=6.4 Hz, 3H), 3.63 (½ ABX, $J_{AB}$=16.6 Hz, $J_{AX}$9.9 Hz, 1H), 3.87 (dd, J=5.9, 2.8 Hz, 1H), 3.99 (½ $A_{AB}$=16.1 Hz, $J_{AX}$=7.7 Hz, 1H), 4.58–4.65 (m, 1H), 4.71–4.76 (m, 1H) 8.19–8.25 (m, 2H), 8.37–8.43 (m 2H), 8.58 (d, J=8.0 Hz, 1H), 9.04 (s, 1H), 9.01 (d, J=8.4 Hz, 1H), 9.63 (s, 1H); I.R. (KBr) 1750, 1580 $cm^{-1}$; U.V. (MOPS BUFFER) $\lambda ext_1$=326 nm, $\epsilon ext_1$=9000; $\lambda ext_2$=336, $\epsilon ext_2$=8800

EXAMPLE 4

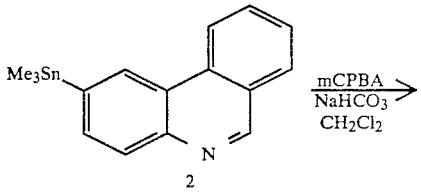

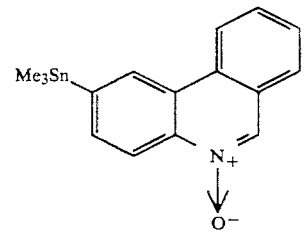

To phenanthridine 2, prepared as described in Example 1 (73.2 mg; 0.214 mmol) in $CH_2Cl_2$ (4.3 mL) cooled to 0° C. under $N_2$ was added aqueous $NaHCO_3$ (1.7 mL; 0.214 mmol; 1 equiv) followed by mCPBA (40.6 mg; 0.235 mmol; 1.1 eq). After allowing the reaction to stir for 2 hours at ambient temperature a 5% aqueous solution of $Na_2S_2O_3$ (5 mL) was added. The reaction mixture was stirred for one hour before being poured into Et$_2$O. The organic layers were washed with H$_2$O (1X), brine (2X), dried over MgSO$_4$, filtered and evaporated. Purification via SiO$_2$ flash column chromatography (100% EtOAc→20% MeOH/EtOAc) provided stannane 6. $^1$H NMR (400 MHz, CDCl$_3$)δ0.42 (s, 9H), 7.66 (t, J=7.8 Hz, 1H), 7.73-7.80 (m, 2H), 7.93 (d, J=8.1 Hz, 1H), 8.56 (d, J=8.4 Hz, 1H), 8.68 (s, 1H), 8.83 (d, J=8.1 Hz, 1H), 8.90 (s, 1H).

EXAMPLE 5

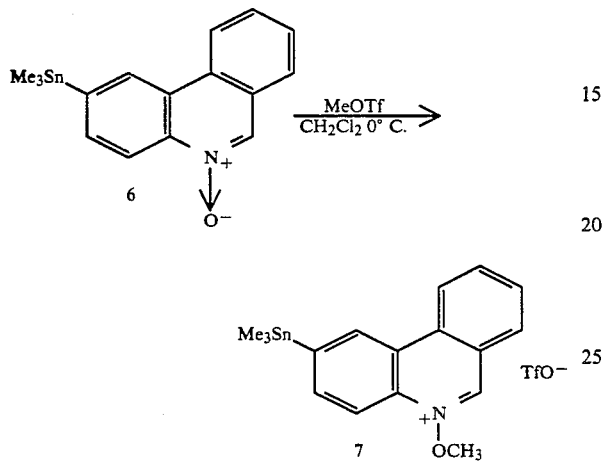

To phenanthridine N-oxide 6 (93 mg; 0.260 mmol) dissolved in anhydrous CH$_2$Cl$_2$ (2.6 mL) cooled to 0° C. under N$_2$ was added MeOTf (32.3 μL; 0.286 mmol; 1.1 equiv). After ½ hour at 0° C., the reaction was quenched by pouring into Et$_2$O and washing with H$_2$O (2x). The organic layers were dried over Na$_2$SO$_4$, filtered and the solvents removed in vacuo to provide the phenanthridine 7.

$^1$H NMR (400 MHz, CDCl$_3$)δ0.49 (s, 9H), 4.73 (s, 3H), 8.04 (t, J=7.3, 1H), 8.19 (d, J=8.4 Hz, 1H), 8.30 (t, J=7.3 Hz, 1H), 8.36 (d, J=8.3 Hz, 1H), 8.82 (d, J=8.4 Hz, 1H), 8.93-8.95 (m, 2H), 10.90 (s, 1H).

EXAMPLE 6

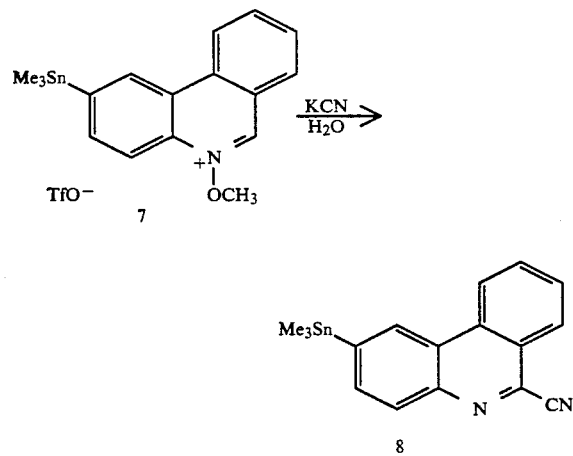

To a suspension of phenanthridine 7 (96.4 mg; 0.185 mmol) in H$_2$O was added KCN (277.7 mg; 0.426 mmol; 2.3 equiv) in H$_2$O. The mixture was heated to reflux until the reaction became homogenous. The reaction mixture was cooled to ambient temperature, poured into Et$_2$O and washed with H$_2$O (1x). The aqueous layer was back extracted with Et$_2$O and the combined ethereal layers then dried over MgSO$_4$, filtered and evaporated in vacuo. Purification via SiO$_2$ flash column chromatography (2% EtOAc/hex) to provide the cyanophenanthridine 8.

$^1$H NMR (400 MHz, CDCl$_2$) δ0.43 (s, 9H), 7.83 (t, J=7.3 Hz, 1H), 7.93-7.99 (m, 2H), 8.17 (d, J=7.9 Hz, 1H), 8.42 (d, J=8.05, 1H), 8.67-8.78 (m, 2H); I.R. (CHCl$_3$) 2240 cm$^{-1}$

EXAMPLE 7

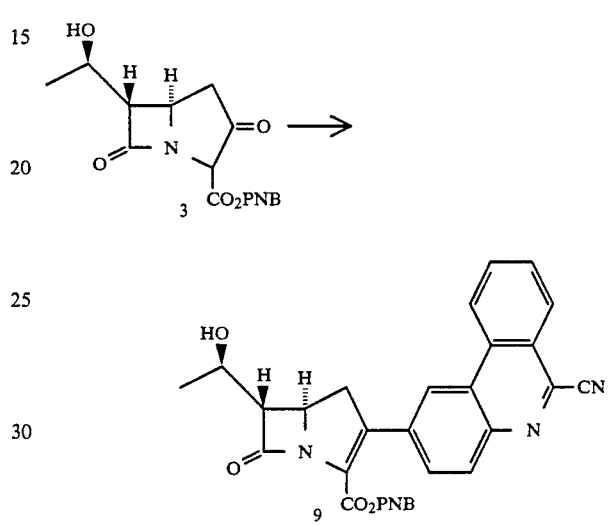

To a stirred solution of the bicyclic β-keto ester 3 (52.7 mg, 0.151 mmol) in dry THF (0.5 mL) at −78° C. under N$_2$ was added diisopropylamine (23.3 μL, 0.166 mmol, 1.1 eq). The resultant yellow mixture was stirred for 10 minutes before trifluoromethanesulfonic anhydride (28.0 μL, 0.166 mmol, 1.1 eq) was added. After 15 minutes the reaction mixture was treated sequentially with anhydrous N-methyl-2-pyrrolidinone (0.5 mL), the Pd$_2$(dba)$_3$•CHCl$_3$ catalyst (2.1 mg, 2.0×10$^{-3}$ mmol, 2.0 mol %), the aryl-stannane 8 (37.0 mg, 0.101 mmol,) and diisopropylammonium chloride (13.9 mg; 0.101 mmol; eq). The low temperature bath was then removed and the reaction vessel was placed in a warm water bath to quickly reach ambient temperature. The resulting wine-red solution was stirred for 20 minutes at ambient temperature.

The reaction was then poured into ether and washed with water (3×) and brine. The organic layer was dried (MgSO$_4$), filtered, and evaporated in vacuo. The residue was dissolved in CH$_2$Cl$_2$ which precipitated the desired product 9.

$^1$H NMR (400 MHz, d$_6$-DMSO) δ1.19 (d, J=6.1 Hz, 3H), 3.33 (½ ABX, obscured by H$_2$O peak in DMSO, 1H), 3.51 (dd, J=6.02, 3.01 Hz, 1H), 3.76 (½ ABX, J$_{AB}$=18.3 Hz, J$_{AX}$=8.11 Hz, 1H), 4.03-4.06 (m, 1H), 4.33 dt, J=10.7, 2.5 Hz, 1H), 5.21 (ABq, J$_{AB}$=13.5 Hz, Δυ$_{AB}$=53.4 Hz, 2H), 7.25 (d, J=8.8 Hz, 2H), 7.69 (d, J=8.7 Hz, 2H), 7.88 (dd, J=8.6, 1.8 Hz, 1H), 7.97 (t, J=7.2 Hz, 1H), 8.05 (t, J=7.6 Hz, 1H), 8.14 (d, J=8.6 Hz, 1H), 8.31 (d, J=7.7 Hz, 1H), 8.84-8.88 (m, 2H); I.R. (KBr) 2240, 1755, 1715, 1610 cm$^{-1}$; U.V. (CH$_3$CN) λ≦355 nm, ε=16,400.

EXAMPLE 8

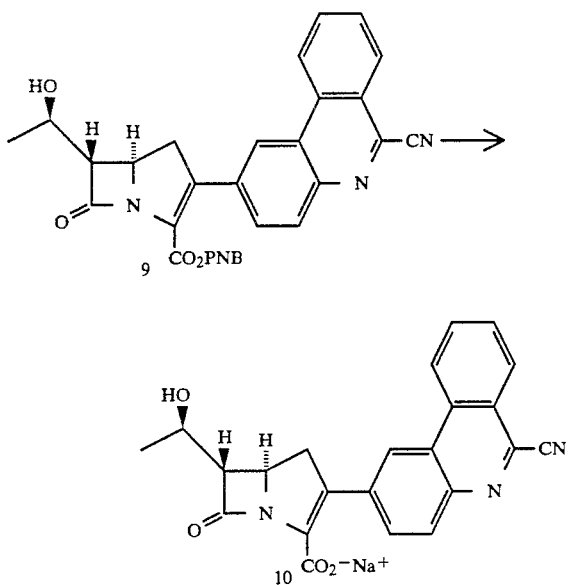

Sodium (5R,6S)-2-(6-cyano-2-phenanthridinyl)-6-(1R-hydroxyethyl)carbapen-2-em-3-carboxylate To a stirred solution of 9 (23 mg, 0.043 mmol) and sodium bicarbonate solution (52 μl, 0.052 mmol, 1.2 eq) in 1:1 acetone/H₂O was added 10% Pd/C catalyst (6.9 mg, 30% wt) and the reaction mixture was hydrogenated under an H₂ balloon at ambient temperature for 45 minutes. The mixture was then filtered trough a pad of celite using water as the eluant, and the acetone solvent from the filtrate was removed in vacuo. The remaining water was then frozen and lyophilized at 0° C. The crude product was redissolved in a minimal amount of H₂O/CH₃CN and purified using Analtech reverse phase prep-plates (3:1 H₂O/CH₃CN) to provide carbapenem 10.

$^1$H NMR(400 MHz, (2:1) D₂O/CD₃CN) δ1.73 (d, J=6.5 Hz, 3H), 3.68 (½ ABX, J$_{AB}$=16.5 Hz, J$_{AX}$=9.8 Hz, 1H), 3.93 (dd, J=5.85, 2.84 Hz, 1H), 4.04 (½ ABX, J$_{AB}$=16.5, J$_{AX}$=8.5 Hz, 1H), 4.64–4.72 (m, 1H), 4.80 (m, obscured by HOD peak, 1H), 8.34–8.39 (complex m, 2H), 8.50–8.54 (complex m, 2H), 8.81 (d, J=8.0 Hz, 1H), 9.0 (d, J=1.6 Hz, 1H), 9.22 (d, J=8.5 Hz, 1H); I.R. (KBr) 1750, 1600 cm$^{-1}$; U.V. (MOPS BUFFER) λext=384 nm, εext=10,000.

EXAMPLE 9

Method A

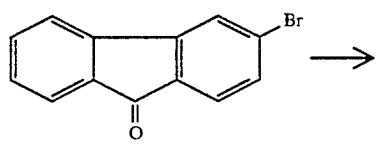

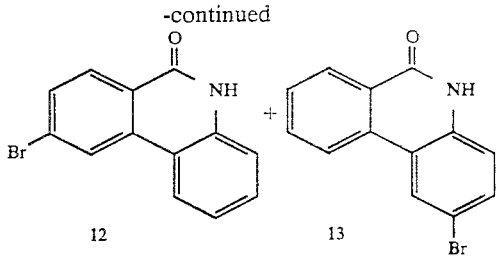

To a stirred solution of 11 (200 mg, 0.77 mmol) in concentrated sulfuric acid (12.9 mL) at 0° C. was added a solution of sodium azide (75.3 mg, 1.16 mmol, 1.5 eq) in water (1 mL). After stirring the resultant black mixture for 24 hours at room temperature, ice-water (10 mL) was added. The reaction mixture was then stirred for 15 minutes, poured into ethyl acetate (200 mL), and washed with saturated sodium bicarbonate solution (2×25 mL), water (2×), and brine. The organic layer was dried (MgSO₄), filtered, and evaporated in vacuo to obtain a mixture of 1:1 inseparable bromo-phenanthridone isomers (12 and 13) in 74% yield (156 mg).

EXAMPLE 10

Method B

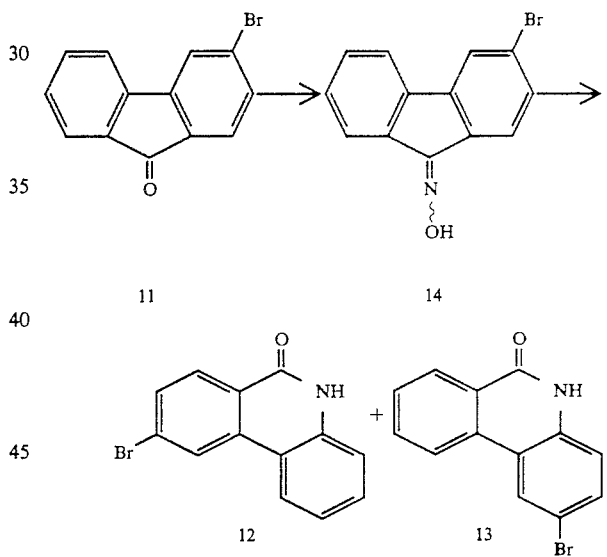

A suspension of 11 (200 mg, 0.77 mmol) and hydroxylamine hydrochloride (161 mg, 2.32 mmol, 3.0 eq) in anhydrous pyridine (7.7 mL) was sonicated to afford dissolution. The homogeneous mixture was then stirred at room temperature for 3.5 hour and poured into ether (100 mL). The ethereal layer was washed with water (1×), 1N HCL solution (4×15 mL), saturated sodium bicarbonate solution (2×15 mL), water (2×), and brine. The organic layer was dried (MgSO₄), filtered, and evaporated in vacuo to afford 200 mg (95%) of the hydroxylamine isomers 14, a white solid. [The hydroxylamine isomers 14 was not characterized and was taken to the next step].

A mixture of 14 (104 mg, 0.38 mmol) in an excess amount of polyphosphoric acid (9 g) was heated to 200° C. After 30 minutes the resultant black paste was dissolved in ice-water (50 mL) and extracted with ethyl acetate (3×50 mL). The combined organic layers were then washed with saturated sodium bicarbonate solution (3×25 mL), water (2x), and brine. The organic layer was dried (MgSO4), filtered, and evaporated in vacuo. The inseparable 1:1 mixture of the phenanthridone isomers (12 and 13) was isolated in 96% yield (100 mg) as a beige solid.

1H-NMR for 12/13 [300 MHz, D6 DMSO, mixture]: δ7.24 to 7.38 (m, 3H), 7.52 (t, J=6.9 Hz, 1H), 7.64 to 7.71 (m, 2H), 7.79 to 7.89 (m, 2H), 8.22 (d, J=8.5 Hz, 1H), 8.32 (d, J=7.4 Hz, 1H), 8.45 (d, J=7.8 Hz, 1H), 8.56 to 8.60 (m, 2H), 8.75 (s, 1H).

IR (KBr): 3020, 2880, 1685, 1610 cm$^{-1}$.

Fast atom bombardment mass spectrum: m/e 274, 276 (calculated MH+ for $C_{13}H_8BrNO$=274, 276).

EXAMPLE 11

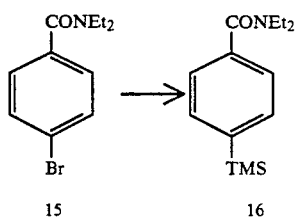

Chlorotrimethylsilane (10.4 mL, 81.9 mmol, 3.0 eq) was added to a stirred solution of 15 (7.0 g, 27.3 mmol) in dry THF (103 mL) at −78° C. under N2. Tert-butyllithium (23.1 mL, 30 mmol, 1.1 eq) was added dropwise at −78° C. over 45 minutes. The reaction mixture was warmed to 0° C. with an ice bath and then quenched with saturated ammonium chloride solution (25 mL). After removal of THF in vacuo the reaction mixture was poured into ether (400 mL) and washed with water, saturated sodium bicarbonate solution (2×50 mL), water, and brine. The ethereal layer was dried (MgSO4), filtered, and evaporated in vacuo. Purification using flash chromatography (20% EtOAc/hex) afforded 5.7 g (87%) of aryl silane 16, a white solid.

1H-NMR for 16 [400 MHz, CDCl3, rotamers]: δ0.24 (s, 9H), 1.08 (broad s, 3H), 1.21 (broad s, 3H), 3.23 (broad s, 2H), 3.51 (broad s, 2H), 7.30 (d, J=8.1 Hz, 2H ), 7.50 ( d, J=8.1 Hz, 2H ).

IR(CHCl3): 3010, 1615 cm$^{-1}$.

EXAMPLE 12

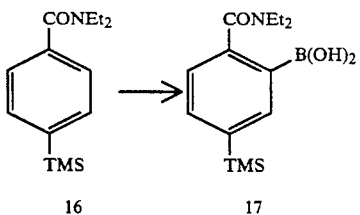

To a stirred solution of N,N,N',N'-tetramethylethylenediamine (2.7 mL, 17.6 mmol, 1.1 eq) in anhydrous THF (100 mL) at −78° C. under N2 was added dropwise sec-butyllithium (13.0 mL, 16.8 mmol, 1.05 eq). After 15 minutes the yellow mixture was treated with a solution of 16 (4.0 g, 16.0 mmol) in dry THF (40 mL), and the resultant red mixture was stirred for 1 hour at −78° C. Trimethylborate (2.0 mL, 17.6 mmol, 1.1 eq) was added dropwise. The reaction flask was warmed to 0° C. with an ice bath and then stirred for 5 minutes. The green reaction mixture was quenched with 8% HCl solution (60 mL), stirred for 10 minutes, and the organic solvent concentrated in vacuo. The mixture was poured into ether and the ethereal layer was washed with water (2x), brine, dried (MgSO4), filtered and evaporated in vacuo. Purification using flash chromatography (5:3:1 EtOAc/acetone/H2O) provided 3.77 g (80%) of boronic acid 17, a white foam.

1H-NMR for 17 [200 MHz, CDCl3, rotamers]: δ0.27 (s, 9H), 0.88 to 1.16 (m, 6H), 3.27 to 3.36 (m, 4H), 7.28 (d, J=6.4 Hz, 1H), 7.52 (d, J=7.6 Hz, 1H), 8.15 (s, 1H).

IR(CHCl3): 2960, 1615, 1601 cm$^{-1}$.

EXAMPLE 13

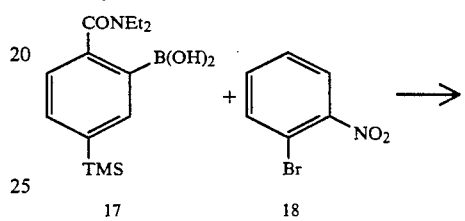

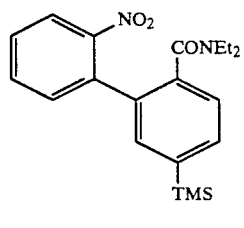

Aqueous sodium carbonate (2.66 mL, 5.32 mmol, 2.0 eq) was added to a stirred solution of 17 (779.3 mg, 2.7 mmol) and tetrakis(triphenylphosphine) palladium (0) (153.7 mg, 5.0 mol %) in toluene (10.6 mL). The resulting two-phase mixture was stirred for 10 minutes under N2 at room temperature. A solution of 18 (590.5 g, 9.6 mmol, 1.1 eq) dissolved in absolute ethanol (5 mL) was added, and the heterogeneous mixture was stirred for 3 hours at reflux under N2. The cooled reaction mixture was poured into ether (175 mi,) and washed with water (1×), saturated sodium carbonate solution (2×25 mL), water (1×), and brine. The organic layer was dried (MgSO4), filtered, and evaporated in vacuo. Purification using flash chromatography (60% EtOAc/hex) provided 812.5 mg (82.5%) of the biphenyl compound 19, a yellow foam.

1H-NMR for 19 [400 MHz, CDCl3, rotamers]: δ0.24 (s, 9H), 0.80(t, J=7.1Hz, 3H), 0.91(t, J=7.1Hz, 3H), 2.80 to 3.67 (broad, 4H), 7.30 to 7.33 (m, 2H), 7.46 (t, J=8.1 Hz, 1H), 7.52 to 7.58 (m, 3H), 7.90 (d, J=8.8 Hz, 1H).

IR (CHCl3): 3000, 2980, 1610, 1580, 1525 cm$^{-1}$.

EXAMPLE 14

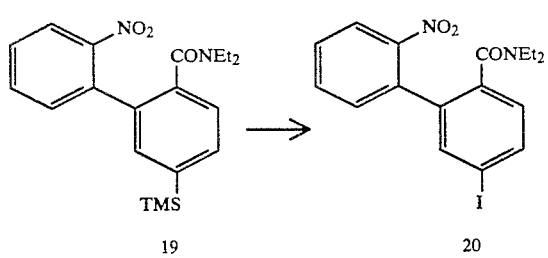

Iodine monochloride in dichloromethane ( 10.9 mL, 10.9 mmol, 5.0 eq) was added dropwise over 0.5 hour to a stirred solution of 19 (812.5 mg, 2.19 mmol ) in dry dichloromethane (10.9 mL). The reaction mixture was then poured in ether (200mL) and washed with saturated sodium thiosulfate solution (2×25 mL), water, saturated bicarbonate solution (2×25 mL), water and brine. The etheral layer was then dried (MgSO4), filtered, and evaporated in vacuo. Purification using flash column chromatography (30% EtOAc/hex) afforded 887.7 mg (95.4%) of 20, a yellow foam.

$^1$H-NMR for 20 [400MHz, CDCl3, rotamers]: S 0.75 (t, J=7.0 Hz, 3H), 0.93 (t, J=7.0 Hz, 3H), 2.82 to 3.60 (broad, 4H), 7.07 (d, J=8.1 Hz, 1H), 7.46 to 7.51 (m, 2H), 7.56 to 7.60 (m, 2H), 7.73 (d, J=8.1 Hz, 1H), 7.97 ( d, J =8.1 Hz, 1H ).

IR (CHCl3): 3000, 2980, 1620, 1580, 1525 cm$^{-1}$.

EXAMPLE 15

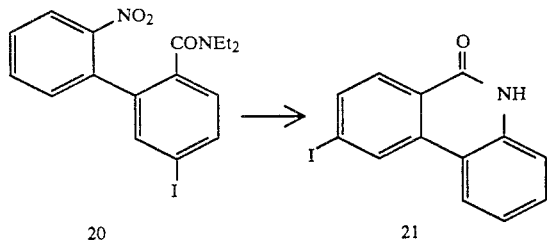

To a stirred solution of .20. (158.0 mg, 0.37 mmol) in 3:2:2 AcOH/EtOH/THF (7.0 mL) was added iron powder (103.8 mg, 1.86 mmol, 5.0 eq), and the reaction mixture was stirred at reflux until a white solid had separated (30 minutes). The reaction mixture was poured into ethyl acetate (200 mL) and washed with saturated sodium bicarbonate solution (1 ×25 mL), water, and brine. The organic layer was dried (MgSO4) filtered and evaporated in vacuo. Chloroform (~10 mL) was added and the product was filtered to afford 119.0 mg (99.5%) of 21, a white solid.

$^1$H-NMR for 21 [400 MHz, D6 DMSO]: δ7.24 (t, J=7.7 Hz, 1H), 7.34 ( d, J=8.1 Hz, 1H), 7.50 ( t, J=7.6 Hz, 1H), 8.42 (d, J=8.1 Hz, 1 H), 8.89 (s, 1H). IR(KBr): 3010, 2990, 2870, 1665, 1600, 1585 cm$^{-1}$.

EXAMPLE 16

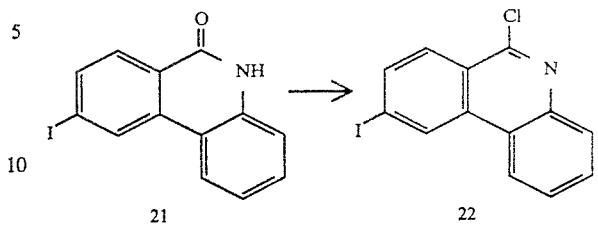

To phenanthridone 21 (50 mg; 0.156 mmol) and PCl5 (32.5 mg; 0.156 mmol; 1.0 eq) was added excess POCl3 (2.5 mL). The reaction was heated to reflux for 5 hours, cooled and quenched by pouring onto ice. The aqueous layer was extracted with CHCl3. The organic layer was dried over MgSO4, filtered and evaporated to provide phenanthridine 22 slightly contaminated with some starting material 21.

$^1$H NMR(400 MHz, CDCl3)δ7.69 (dt, J=8.2, 1.3 Hz, 1H), 7.76 (dr, J=7.2, 1.4 H$_z$, 1H), 8.02-8.08 (m, 2H), 8.16 (d, 8.8 Hz, 1H), 8.45 (d, 7.1 Hz, 1H), 8.97 (d, J=1.6 Hz, 1H)

EXAMPLE 17

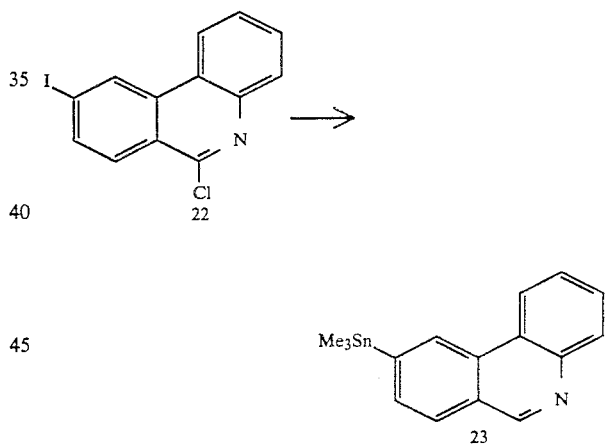

To phenanthridine 22 (170 mg; 0.50 mmol) in toluene (5 mL) was added Me3SnSnMe3 (180 mg; 0.55 mmol; 1.1 eq), Pd(PPh3)4 (29 mg; 0.025 mmol; 5 mol %) and triphenylphosphine (3.9 mg; 0.015 mmol; 3 mol %). After bubbling N2 through the reaction mixture for 15 minutes, the vessel was heated to reflux for 3 hours. The reaction was cooled, poured into Et2O and washed with H2O (1×), saturated NaHCO3 solution (1×), H2O (2×) and brine. The organic layer was dried (MgSO4), filtered and evaporated. Purification by flash chromatography (20% EtoAc/hex) provided 23.

$^1$H NMR (400 MHz, CDCl3) δ0.42 (s, 9H), 7.65-7.75 (m, 2H), 7.81 (d, J=7.7 Hz, 1H), 7.96 (d, J=7.7 Hz, 1H), 8.17 (dd, J=8.1, 1.3 Hz, 1H), 8.63 (dd, 8.1, 1.4 Hz, 1H), 8.74 (s, 1H), 9.25 (s, 1H).

EXAMPLE 18

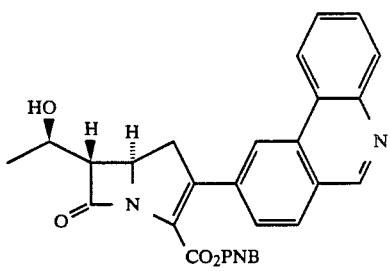

Compound 24 was prepared by employing the procedure described in Example 2, but substituting the stannane prepared as described in Example 17 for the regio isomeric stannane % and after stirring for 4 days.

$^1$H NMR (400 MHz, CDCl$_3$)δ1.40 (d, J=6.2 Hz, 3H), 3.31–3.45 (complex m, 3H), 4.29–4.35 (m, 1H), 4.44 (dr, J=9.7, 2.8 Hz, 1H), 5.23 (ABq, J$_{AB}$=13.5, Δυ$_{AB}$=72.1 Hz, 2H), 7.32 (d, J=8.7 Hz, 2H), 7.59–7.68 (m, 2H), 7.74 (t, J=7.0 Hz, 1H), 7.93 (d, J=8.7 Hz, 1H), 7.99 (d, J=8.3 Hz, 1H), 8.17 (d, J=7.3 Hz, 1H), 8.39 (d, J=7.7 Hz, 1H), 8.53 (s, 1H) 9.24 (s, 1H); I.R. (CHCl$_3$) 1775, 1725, 1600, 1520 cm$^{-1}$; U.V. (CH$_3$CN) λ=323 nm, ε=9900

EXAMPLE 19

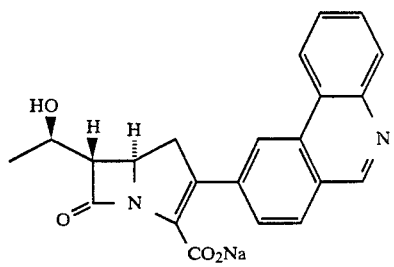

Sodium (5R, 6S)-2-(9-phenanthridinyl)-6-(1R-hydroxyethyl)carbapen-2-em-3-carboxylate Compound 25 was prepared by the procedure described in Example 3 but substituting the carbapenem prepared as described in Example 18 for carbapenem 4.

$^1$H NMR (400 MHz, (2:1) D$_2$O/CD$_3$CN) δ1.65 (d, J=6.6 Hz, 3H), 3.60 (½ ABX, J$_{AB}$=16.5 Hz, J$_{AX}$=2.2Hz, 1H), 3.86 (dd, J=5.9, 2.7 Hz, 1H), 3.97 (½ ABX, J$_{AB}$=16.5 Hz, J$_{AX}$=8.5 Hz, 1H), 4.55–4.64 (m, 1H), 4.70 (dt, J=9.2, 2.5 Hz, 1H), 8.11–8.22 (complex m, 3H), 8.43–8.49 (m, 2H), 8.98 (s, 1H), 9.05 (d, J=8.1 Hz, 1H), 9.57 (brood s, 1H): I.R. (KBr) 1750, 1600 cm$^{-1}$; U.V. (MOPS BUFFER) λ$_{ext}$=338 nm, ε$_{ext}$=8700.

EXAMPLE 20

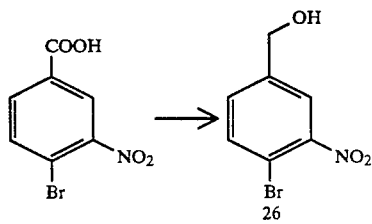

To a stirred solution of 4-bromo-3-nitrobenzoic acid (5.0 g, 20.3 mmol) in dry THF (40.6 mL) under N$_2$ at room temperature was added dropwise the borane-tetrahydrofuran complex (40.6 mL, 40.6 mmol, 2.0 eq). After stirring at reflux for 1 hour the reaction mixture was quenched with dropwise addition of triethylamine (1 mL) in methanol (50 mL) at 0° C. The solvent was then removed in vacuo to give crude 4. Purification using flash chromatography (30% EtOAc/hex) provided 4.5 g (96%) of 26, an off-white solid.

$^1$H-NMR for 26 [400 MHz, CDCl$_3$]: δ1.86 (t, J=5.8 Hz, 1H), 4.74 (d, J=5.8 Hz, 2H), 7.41 (dd, J=8.3, 2.1Hz, 1H), 7.70 (d, J=8.3 Hz, 1H), 7.85 (s, 1H).

IR(CHCl$_3$): 3605, 3500 to 3200, 3010, 2880, 1605, 1535, 1355 cm$^{-1}$.

EXAMPLE 21

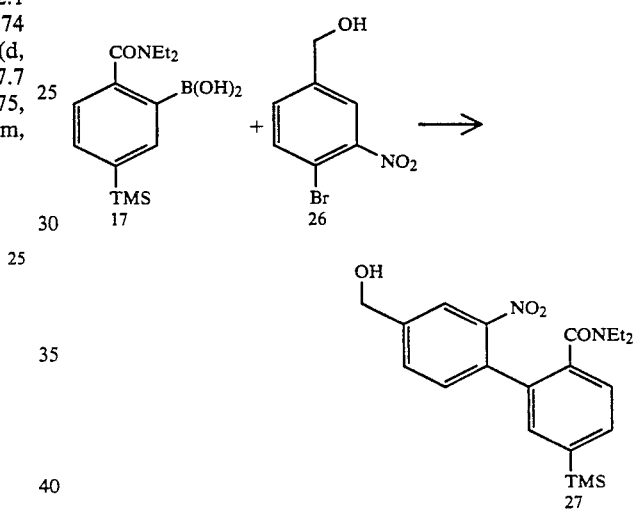

Aqueous sodium carbonate (8.7 mL, 17.4 mmol, 2.0 eq) was added to a stirred solution of 17 (2.0 g, 8.7 mmol) and tetrakis(triphenylphosphine) palladium (O) (502.8 mg, 5.0 mol %) in toluene (33.5 mL). The resulting two-phase mixture was stirred for 10 minutes under N$_2$ at room temperature. A solution of 26 (2.8 g, 9.6 mmol, 1.1 eq) dissolved in absolute ethanol (9.6 mL) was added, and the heterogeneous mixture was stirred for 3 hours at reflux under N$_2$. The cooled reaction mixture was poured into ether (175 mL) and washed with water (1X), saturated sodium carbonate solution (2×25 mL), water (1×), and brine. The organic layer was dried (MgSO$_4$), filtered, and evaporated in vacuo. Purification using flash chromatography (60% EtOAc/hex) provided 2.9 g (83%) of the biphenyl compound 27, a yellow foam.

$^1$H-NMR for 27 [400 MHz, CDCl$_3$, rotamers]: δ 0.24 (s, 9H), 0.87 (t, J=7.1 Hz, 3H), 0.94 (t, J=7.1 Hz, 3H), 2.40 (broad s, 1H), 2.72 to 3.65 (broad, 4H), 4.76 (s, 2H), 7.30 to 7.32 (m, 2H), 7.51 to 7.56 (m, 3H), 7.93 ( s, 1H).

IR(CHCl$_3$): 3360, 3520 to 3300, 2990, 1620, 1605, 1530 cm$^{-1}$.

EXAMPLE 22

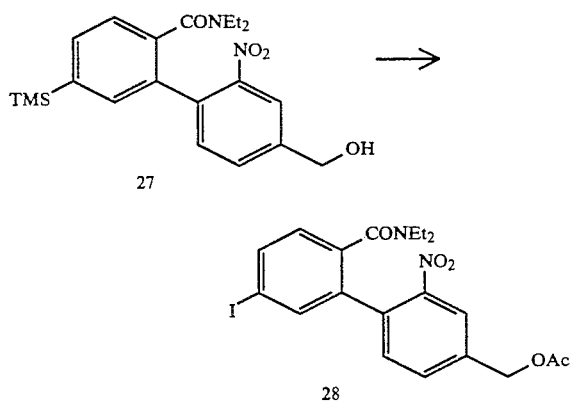

Acetic anhydride (6.8 mL, 72.4 mmol, 10.0 eq) was added to a stirred solution of 27 (2.9 g, 7.24 mmol) in dry pyridine (36 mL). The reaction mixture was stirred for 25 minutes at room temperature under $N_2$. The solvent was removed in vacuo and the residual oil azeotroped from toluene. The crude acetate was redissolved in dry dichloromethane (20 mL), and a 1.0M solution of iodine monochloride in dichloromethane (33 mL, 33.3 mmol, 4.6 eq) was added dropwise over 1 hour using an addition funnel. The reaction mixture was then poured into ether (250 mL) and the organic layer was washed with saturated sodium thiosulfate solution (3 ×30 mL), water (1×), saturated sodium bicarbonate solution (1×30 mL), water (1×), and brine. The organic layer was dried (MgSO$_4$), filtered, and evaporated in vacuo to afford 3.6 g (quantitative yield) of 28, a yellow oil.

$^1$H-NMR for 28 [400 MHz, CDCl$_3$, rotamers]: δ 0.81 (t, J=7.1 Hz, 3H), 0.98 (t, J=7.1 Hz, 3H), 2.14 (s, 3H), 2.78 to 3.65 (broad, 4H), 5.17 (s, 2H), 7.08 (d, J=8.1 Hz, 1H), 7.49 to 7.61 (m, 3H), 7.76 (d, J=8.0 Hz, 1H), 7.97 (s, 1H).

IR(CHCl$_3$): 3010, 1745, 1610, 1530 cm$^{-1}$.

EXAMPLE 23

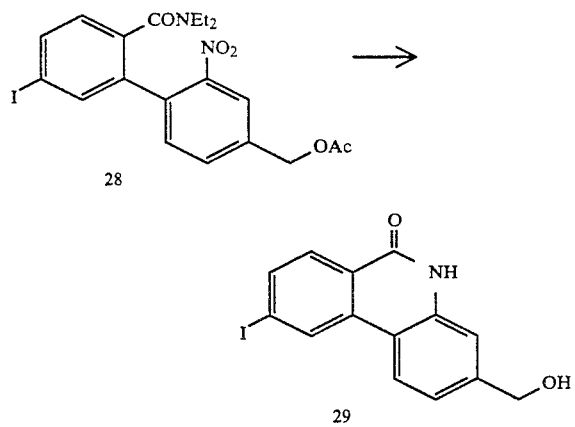

A solution of 25% sodium methoxide in methanol (0.53 mL, 2.4 mmol, 1.1 eq) was added to a stirred solution of 28 (1.1 g, 2.2 mmol) in dry methanol (11.0 mL). The reaction mixture was stirred for 10 minutes at room temperature under $N_2$. Acetic acid (6.0 mL) and dry tetrahydrofuran (11.0 mL) were then added. Iron powder (371.9 mg, 6.7 mmol, 3.0 eq) was added next, and the reaction mixture was stirred at reflux until a white solid had separated (approximately 15 minutes). The reaction mixture was cooled, poured into ice water (250 mL), and the solid filtered. The crude cyclized product was redissolved in hot ethanol (250 mL), filtered through a hot-sintered glass funnel, and the solvent removed in vacuo. Recrystallization from ethanol provided 501 mg (64%) of the cyclized amide 29, a white fluffy solid.

$^1$H-NMR for 29 [400 MHz, d$_6$-DMSO]: δ4.57 (s, 2H), 5.36 (t, J=5.7 Hz, 1H), 7.16 (d, J=8.2 Hz, 1H), 7.33 (s, 1H), 7.93 (d, J=8.4Hz, 1H), 8.00 (d, J=8.4 Hz, 1H), 8.35 (d, J=8.4 Hz, 1H), 8.85 (s,1H), 11.74 (s,1H).

IR (KBr): 1670, 1601 cm$^{-1}$.

EXAMPLE 24

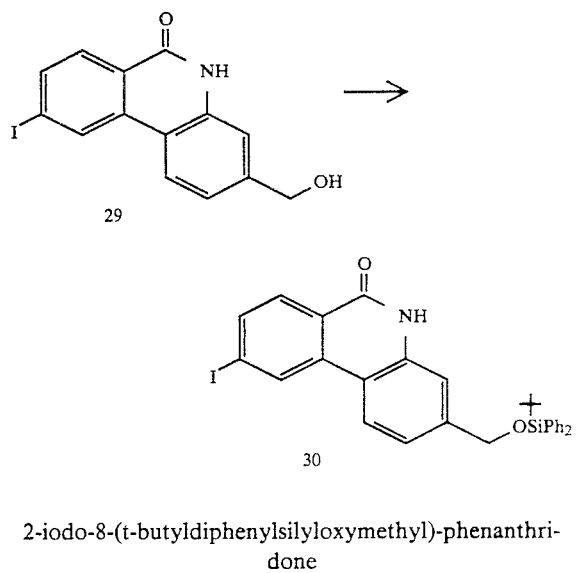

2-iodo-8-(t-butyldiphenylsilyloxymethyl)-phenanthridone

To a solution of 2-iodo-8-(hydroxymethyl) phenanthridone 29 and t-butyldiphenylsilyl chloride in CH$_2$Cl$_2$ and THF are added triethylamine followed by 4-dimethylaminopyridine. After stirring at room temperature until chromatographic analysis indicates complete reaction, the solution is poured into ethyl ether and washed successively with sat. NaHCO$_3$, H$_2$O, and brine. Drying (Na$_2$SO$_4$) and evaporation provides the crude product which is purified by flash chromatography to provide the title compound 30.

EXAMPLE 25

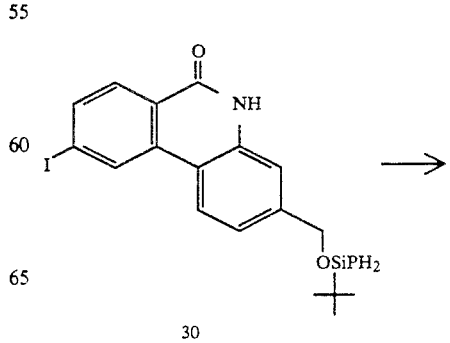

-continued

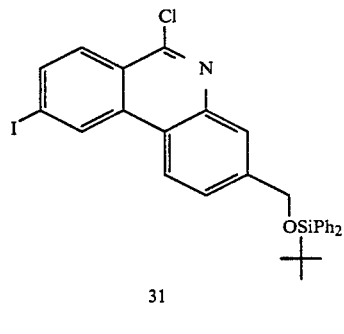
31

To a mixture of phenanthridone 30 and PCl₅ is added a molar excess of POCl₃. The reaction is heated to reflux until chromatographic analysis indicates complete reaction, cooled and quenched by pouring onto ice. The aqueous layer is extracted with CHCl₃. The organic layer is dried over MgSO₄, filtered and evaporated to provide phenanthridine 31.

EXAMPLE 26

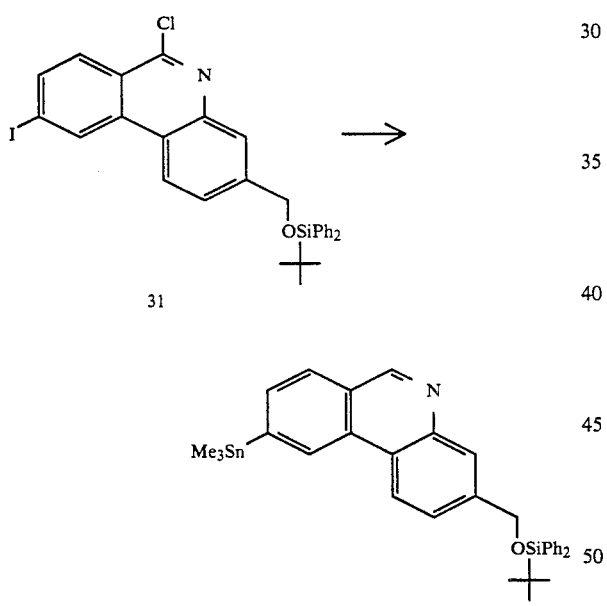

To a solution of phenanthridine 31 in toluene is added Me₃SnSnMe₃, Pd(PPh₃)₄ and triphenyl phosphine. After N₂ is bubbled through the reaction mixture for 15 minutes, the vessel is heated to reflux until chromatographic analysis indicates complete reaction. The reaction is cooled, poured into ether and the organic solution is washed with H₂O (1×), saturated NaHCO₃ solution (1×), H₂O (2×) and brine. The organic layer is dried over MgSO₄, filtered and evaporated to provide the crude product. The crude product is purified by flash chromatography to provide the compound 32.

EXAMPLE 27

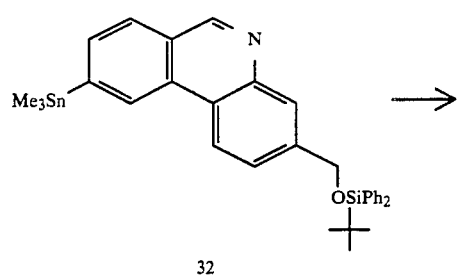
32

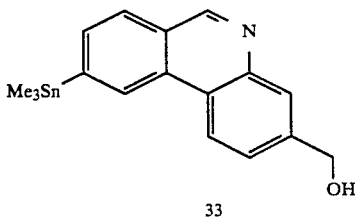
33

To a solution of the phenanthridine 32 is THF is added a 1.0M solution of nBu₄NF in THF. The reaction solution is stirred until chromatographic analysis indicates complete reaction and then poured into EtOAC. The organic solution is washed with saturated aqueous NaHCO₃ (2×) and brine, then is dried over MgSO₄ and filtered. The solution is concentrated in vacuo and purified by flash chromatography to provide the phenanthridine 33.

EXAMPLE 28

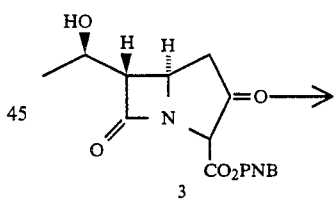
3

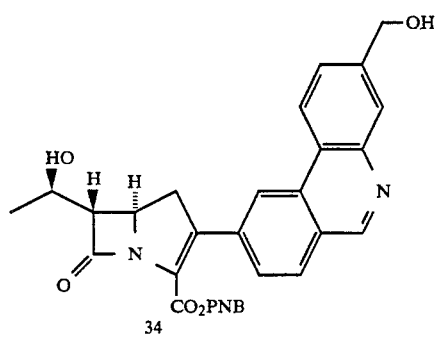
34

Employing the procedure described in Example 2, but substituting the hydroxymethylphenanthridinyl stannane prepared as described in Example 27 for the stannane 2, provides the carbapenem 34.

EXAMPLE 29

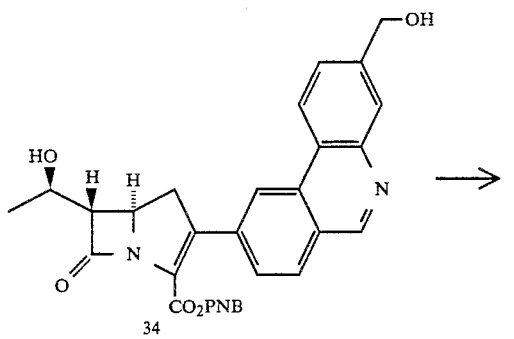

↓

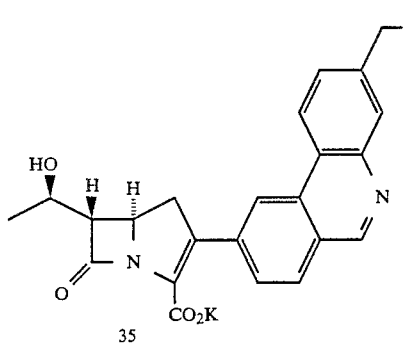

Employing the procedure described in Example 3, but substituting the hydroxymethylphenanthridinyl carbapenem 34 prepared as described in Example 28 for the carbapenem 4, provides the carbapenem 35.

What is claimed is:

1. A compound of the formula:

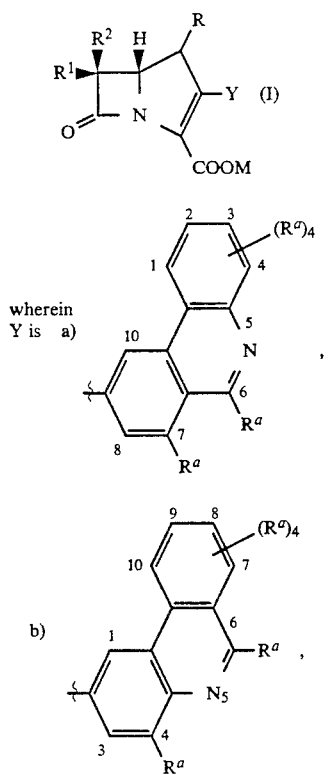

wherein Y is a)

b)

c) or d) ;

R is H or $CH_3$;

$R^1$ and $R^2$ are independently H, $CH_3$—, $CH_3CH_2$—, $(CH_3)_2CH$—, $HOCH_2$—, $CH_3CH(OH)$—, $(CH_3)_2C(OH)$—, $FCH_2CH(OH)$—, $F_2CHCH(OH)$—, $F_3CCH(OH)$—, $CH_3CH(F)$—, $CH_3CF_2$—, or $(CH_3)_2C(F)$—;

$R^a$ are independently selected from the group consisting of hydrogen and the radicals set out below, provided that not more than four $R^a$ radicals are other than hydrogen:

a) a trifluoromethyl group: —$CF_3$;
b) a halogen atom: —Br, —Cl, —F, or —I;
c) $C_1$-$C_4$ alkoxy radical: —$OC_{1-4}$ alkyl, wherein the alkyl is optionally mono-substituted by $R^q$, where $R^1$ is a member selected from the group consisting of —OH, —$OCH_3$, —CN, —C(O)$NH_2$, —OC(O)$NH_2$, CHO, —OC(O)N($CH_3$)$_2$, —$SO_2NH_2$, —$SO_2N(CH_3)_2$, —$SOCH_3$, —$SO_2CH_3$, —F, —$CF_3$, —COO$M^a$, where $M^a$ is hydrogen, alkali metal, methyl or phenyl, tetrazolyl, where the point of attachment is the carbon atom of the tetrazole ring and one of the nitrogen atoms is mono-substituted by $M^a$ as defined above, and —$SO_3M^b$, where $M^b$ is hydrogen or an alkali metal;

d) a hydroxy group: —OH;
e) a carbonyloxy radical: —O(C=O)$R^s$, where $R^s$ is $C_{1-4}$ alkyl or phenyl, each of which is optionally mono-substituted by $R^q$ as defined above;
f) a carbamoyloxy radical: —O(C=O)N($R^y$)$R^z$ where $R^y$ and $R^z$ are independently H, $C_{1-4}$ alkyl, optionally mono-substituted by $R^q$ as defined above, together a 3- to 5-membered alkylidene radical to form a ring, optionally substituted with $R^q$ as defined above, or together a 2- to 4-membered alkylidene radical, interrupted by —O—, —S—, —S(O)— or —S(O)$_2$— to form a ring, where the ring is optionally mono-substituted with Rq as defined above;

g) a sulfur radical: —S(O)$_n$—$R^s$ where n=0-2, and $R^s$ is defined above;
h) a sulfamoyl group: —$SO_2N(R^y)R^z$ where $R^y$ and $R^z$ are as defined above;
i) azido: $N_3$
j) a formamido group: —N($R^t$)(C=O)H, where $R^t$ is H or $C_{1-4}$ alkyl, and the alkyl thereof is optionally mono-substituted by $R^q$ as defined above;

k) a $(C_1-C_4$ alkyl)carbonylamino radical: $-N(R^t)(-C=O)C_{1-4}$ alkyl, where $R^t$ is as defined above, and the alkyl group is also optionally mono-substituted by $R^q$ as defined above;

l) a $(C_1-C_4$ alkoxy) carbonylamino radical: $-N(R^t)(C=O)OC_{1-4}$ alkyl, where $R^t$ is as defined above, and the alkyl group is also optionally mono-substituted by $R^q$ as defined above;

m) a ureido group: $-N(R^t)(C=)N(R^y)R^z$ where $R^t$, $R^y$ and $R^z$ are as defined above;

n) a sulfonamido group: $-N(R^t)SO_2R^s$, where $R^s$ and $R^t$ are as defined above;

o) a cyano group: $-CN$;

p) a formyl or acetalized formyl radical: $-(C=O)H$ or $-CH(OCH_3)_2$;

q) $(C_1-C_4$ alkyl)carbonyl radical wherein the carbonyl is acetalized: $-C(OCH_3)_2C_{1-4}$ alkyl, where the alkyl is optionally mono-substituted by $R^q$ as defined above;

r) carbonyl radical: $-(C=O)R^s$, where $R^s$ is as defined above;

s) a hydroximinomethyl radical in which the oxygen or carbon atom is optionally substituted by a $C_1-C_4$ alkyl group: $-(C=NOR^z)R^y$ where $R^y$ and $R^z$ are as defined above, except they may not be joined together to form a ring;

t) a $(C_1-C_4$ alkoxy)carbonyl radical: $-(C=O)OC_{1-4}$alkyl, where the alkyl is optionally mono-substituted by $R^q$ as defined above;

u) a carbamoyl radical: $-(C=O)N(R^y)R^z$ where $R^y$ and $R^z$ are as defined above;

v) an N-hydroxycarbamoyl or N($C_1-C_4$ alkoxy)-carbamoyl radical in which the nitrogen atom may be additionally substituted by a $C_1-C_4$ alkyl group: $-(C=O)-N(OR^y)R^z$ where $R^y$ and $R^z$ are as defined above, except they may not be joined together to form a ring;

w) a thiocarbamoyl group: $-(C=S)N(R^y)(R^z)$ where $R^y$ and $R^z$ are as defined above;

x) carboxyl: $-COOM^b$, where $M^b$ is as defied above;

y) thiocyanate: $-SNC$;

z) trifluoromethylthio: $-SCF_3$;

aa) tetrazolyl, where the point of attachment is the carbon atom of the tetrazole ring and one of the nitrogen atoms is mono-substituted by hydrogen, an alkali metal or a $C_1-C_4$ alkyl optionally substituted by $R^q$ as defined above;

ab) an anionic function selected from the group consisting of: phosphono $[P=O(OM^b)_2]$; alkylposphono $\{P=O(OM^b)-[O(C_1-C_4$ alkyl$)]\}$; alkylphosphinyl $[P=(OM^b)-(C_1-C_4alkyl)]$; phosphoramido $[P=(OM^b)N(R^y)R^z$ and $P=O-(OM^b)NHR^x]$; sulfino $(SO_2M^b)$; sulfo $(SO_3M^b)$; acylsulfonamides selected from the structures $CONM^bSO_2R^x$, $CONM^bSO_2N(R^y)R^z$, $SO_2NM^bCON(R^y)R^z$; and $SO_2NM^bCN$, where $R^x$ is phenyl or heteroaryl, where heteroaryl is a monocyclic aromatic hydrocarbon group having 5 or 6 ring atoms, in which a carbon atom is the point of attachment, in which one of the carbon atoms has been replaced by a nitrogen atom, in which one additional carbon atom is optionally replaced by a heteroatom selected from O or S, and in which from 1 to 2 additional carbon atoms are optionally replaced by a nitrogen heteroatom, and where the phenyl and heteroaryl are optionally mono-substituted by $R^q$, as defined above; $M^b$ is as defined above; and $R^y$ and $R^z$ are as defined above;

ac) $C_5-C_7$ cycloalkyl group in which one of the carbon atoms in the ring is replaced by a heteroatom selected from O, S, NH or N($C_1-C_4$ alkyl) and in which one additional carbon atom may be replaced by NH or N($C_1-C_4$ alkyl), and in which at least one carbon atom adjacent to each nitrogen heteroatom has both of its attached hydrogen atoms replaced by one oxygen thus forming a carbonyl moiety and there are one or two carbonyl moieties present in te ring;

ad) $C_2-C_4$ alkenyl radical, optionally mono-substituted by one of the substituents a) to ac) above and phenyl which is optionally substituted by $R^q$ as defined above;

ae) $C_2-C_4$ alkynyl radical, optionally mono-substituted by one of the substituents a) to ac) above;

af) $C_1-C_4$ alkyl radical;

ag) $C_1-C_4$ alkyl mono-substituted by one of the substituents a)-ac) above;

ah) a 2-oxazolidinonyl moiety in which the point of attachment is the nitrogen atom of the oxazolidinone ring, the ring oxygen atom is optionally replaced by a heteroatom selected from —S— an $NR^t$, where $R^t$ is as defined above, and one of the saturated carbon atoms of the oxazolidinone ring is optionally mono-substituted by one of the substituents a) to ag) above; and M is selected from:
 i) hydrogen;
 ii) a pharmaceutically acceptable esterifying group or removable carboxyl protecting group; or
 iii) an alkali metal or other pharmaceutically acceptable cation.

2. The compound of claim 1, wherein $R^1$ is hydrogen and $R^2$ is (R)—$CH_3CH(OH)$— or (R)—$CH_3CH(F)$—.

3. The compound of claim 2, wherein Y is:

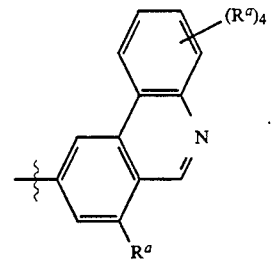

4. The compound of claim 2, wherein Y is:

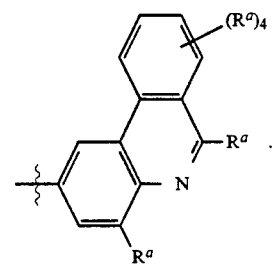

5. The compound of claim 2 wherein one to three $R^a$ substituents are selected from:

| | |
|---|---|
| —OCH₃ | |
| —OCH₂CH₂OH | —OCH₂CO₂CH₃ |
| —F | —CF₃ |
| —Br | —Cl |
| —OH | —I |
| —OCONH₂ | —OCOCH₃ |
| —SOCH₃ | —SCH₃ |
| —SCH₂CH₂OH | —SO₂CH₃ |
| —SO₂NH₂ | —SOCH₂CH₂OH |
| —NHCHO | —SO₂N(CH₃)₂ |
| —NHCO₂CH₃ | —NHCOCH₃ |
| —CN | —NHSO₂CH₃ |
| —COCH₃ | —CHO |
| —CH=NOH | —COCH₂OH |
| —CH=NOCH₂CO₂CH₃ | —CH=NOCH₃ |
| —SO₂CH₂CH₂OH | —CH=NOCMe₂CO₂CH₃ |
| —CH=NOCMe₂CO₂Me | —CO₂CH₂CH₂OH |
| —CONH₂ | —CONHCH₃ |
| —CON(CH₃)₂ | —CONHCH₂CN |
| —CONHCH₂CONH₂ | —CONHCH₂CO₂CH₃ |
| —CONHOH | —CONHCH₃ |
| -tetrazolyl | —CO₂CH₃ |
| —SCF₃ | —PO₃CH₃H |
| —CONHSO₂Ph | —CONHSO₂NH₂ |
| —SO₃CH₃ | —SO₂NHCN |
| —SO₂NHCONH₂ | —CH=CHCN |

-continued

| | |
|---|---|
| —CH=CHCONH₂ | —CH=CHCO₂CH₃ |
| —C≡C—CONH₂ | —C≡C—CN |
| —CH₂OH | —CH₂N₃ |
| —CH₂CO₂CH₃ and | —CH₂I. |

6. The compound according to claim 1, wherein the structural formula is:

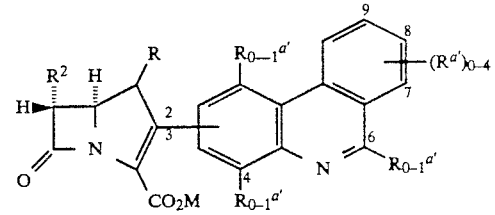

and the substituents $R^{a'}$, which is $R^a$ when it is not hydrogen, R, $R^2$ and M and the attachment point (att pt), which is the position on the phenanthridine ring where the carbapenem nucleus is attached, are as defined in Table I below:

TABLE I

| Att pt | R | $R^2$ | M | $R^{a'}$ | $R^{a'}$ position |
|---|---|---|---|---|---|
| 2 | —H | (R)—CH(OH)CH₃ | —Na⁺ | —OCH₃ | 4, 7 |
| 2 | —H | (R)—CH(OH)CH₃ | —Na⁺ | —OCH₂CO₂Me | 4 |
| 3 | —H | (R)—CH(OH)CH₃ | —H | —OCH₂CH₂OH | 8 |
| 2 | —H | (R)—CH(OH)CH₃ | —Na⁺ | —CF₃ | 7 |
| 2 | —H | (R)—CH(OH)CH₃ | —Na⁺ | —F | 7 |
| 3 | —H | (R)—CH(OH)CH₃ | —Na⁺ | —Cl | 8 |
| 3 | —H | (R)—CH(OH)CH₃ | —Na⁺ | —Br | 7 |
| 2 | —H | (R)—CH(OH)CH₃ | —Na⁺ | —F | 4, 7, 8 |
| 2 | —H | (R)—CH(OH)CH₃ | —Na⁺ | —OH | 7, 8 |
| 3 | —CH₃ | (R)—CH(OH)CH₃ | —H | —OCOCH₃ | 8 |
| 2 | —H | (R)—CH(OH)CH₃ | —Na⁺ | —OCONH₂ | 8 |
| 2 | —H | (R)—CH(OH)CH₃ | —Na⁺ | —SCH₃ | 4 |
| 2 | —H | (R)—CH(F)CH₃ | —Na⁺ | —SOCH₃ | 4 |
| 3 | —H | (R)—CH(OH)CH₃ | —Na⁺ | —SO₂CH₃ | 8 |
| 3 | —H | (R)—CH(OH)CH₃ | —Na⁺ | —SCH₂CH₂OH | 8 |
| 2 | —H | (R)—CH(OH)CH₃ | —Na⁺ | —SOCH₂CH₂OH | 7 |
| 2 | —H | (R)—CH(OH)CH₃ | —Na⁺ | —SCH₂CONH₂ | 7 |
| 3 | —H | (R)—CH(OH)CH₃ | —Na⁺ | —SO₂NH₂ | 8 |
| 2 | —H | (R)—CH(OH)CH₃ | —Na⁺ | —SO₂N(CH₃)₂ | 7, 8 |
| 2 | —H | CF₂CH₃ | —Na⁺ | —NHCHO | 7, 8 |
| 3 | —H | (R)—CH(OH)CH₃ | —Na⁺ | —NHCOCH₃ | 6 |
| 3 | —H | (R)—CH(OH)CH₃ | —H | —NHCO₂CH₃ | 10 |
| 3 | —H | (R)—CH(OH)CH₃ | —Na⁺ | —NHSO₂CH₃ | 7 |
| 2 | —H | (R)—CH(F)CH₃ | —Na⁺ | —CN | 6 |
| 3 | —H | (R)—CH(F)CH₃ | —Na⁺ | —CHO | 9 |
| 2 | —H | (R)—CH(OH)CH₃ | —Na⁺ | —COCH₃ | 10 |
| 2 | —H | (R)—CH(OH)CH₃ | —Na⁺ | —COCH₂OH | 8 |
| 3 | —CH₃ | (R)—CH(OH)CH₃ | —Na⁺ | —CH=NOH | 8 |
| 3 | —H | (R)—CH(OH)CH₃ | —Na⁺ | —CH=NOCH₃ | 7 |
| 3 | —CH₃ | (R)—CH(OH)CH₃ | —H | —CH=NOCH₂CO₂Me | 9 |
| 2 | —H | (R)—CH(OH)CH₃ | —Na⁺ | —CH=NOCMe₂CO₂Me | 6 |
| 2 | —H | (R)—CH(OH)CH₃ | —Na⁺ | —CH=NOCMe₂CO₂Me | 8 |
| 2 | —H | (R)—CH(OH)CH₃ | —Na⁺ | —CO₂CH₂CH₂OH | 7 |
| 3 | —H | (R)—CH(F)CH₃ | —Na⁺ | —CONH₂ | 7, 8 |
| 3 | —H | (R)—CH(OH)CH₃ | —Na⁺ | —CONHCH₃ | 9 |
| 3 | —H | (R)—CH(OH)CH₃ | —Na⁺ | —CON(CH₃)₂ | 8 |
| 2 | —H | (R)—CH(OH)CH₃ | —K⁺ | —CONHCH₂CN | 4 |
| 2 | —H | (R)—CH(OH)CH₃ | —K⁺ | —CONHCH₂CONH₂ | 8 |
| 3 | —H | (R)—CH(OH)CH₃ | —K⁺ | —CONHCH₂CO₂Me | 7 |
| 2 | —H | (R)—CH(OH)CH₃ | —Na⁺ | —CONHOH | 9 |
| 3 | —H | (R)—CH(OH)CH₃ | —Na⁺ | —CONHOCH₃ | 7 |
| 2 | —H | (R)—CH(OH)CH₃ | —Na⁺ | -tetrazolyl | 8 |
| 3 | —H | (R)—CH(OH)CH₃ | —Na⁺ | —CO₂Me | 7 |
| 2 | —H | (R)—CH(OH)CH₃ | —Na⁺ | —SCF₃ | 4 |
| 2 | —H | (R)—CH(OH)CH₃ | —H | —PO₃MeH | 8 |
| 2 | —H | (R)—CH(OH)CH₃ | —Na⁺ | —CONHSO₂Ph | 10 |
| 2 | —H | (R)—CH(OH)CH₃ | —Na⁺ | —CONHSO₂NH₂ | 7 |
| 3 | —H | (R)—CH(OH)CH₃ | —K⁺ | —SO₃Me | 8 |
| 3 | —H | (R)—CH(OH)CH₃ | —Na⁺ | —SO₂NHCN | 8 |
| 2 | —H | (R)—CH(F)CH₃ | —Na⁺ | —SO₂NHCONH₂ | 7 |

TABLE I-continued

| Att pt | R | R² | M | R^{a'} | R^{a'} position |
|---|---|---|---|---|---|
| 2 | —H | (R)—CH(OH)CH₃ | —Na⁺ | —CH=CHCN | 7 |
| 2 | —H | (R)—CH(OH)CH₃ | —Na⁺ | —CH=CHCONH₂ | 8 |
| 3 | —H | (R)—CH(OH)CH₃ | —Na⁺ | —CH=CHCO₂Me | 9 |
| 3 | —H | (R)—CH(OH)CH₃ | —Na⁺ | —C≡C—CONH₂ | 8 |
| 3 | —CH₃ | (R)—CH(OH)CH₃ | —Na⁺ | —C≡C—CN | 7 |
| 2 | —H | (R)—CH(OH)CH₃ | —K⁺ | —CH₂OH | 6 |
| 2 | —H | (R)—CH(OH)CH₃ | —K⁺ | —CH₂N₃ | 7 |
| 3 | —H | (R)—CH(OH)CH₃ | —Na⁺ | —CH₂CO₂Me | 7 |
| 2 | H | (R)—CH(OH)CH₃ | —Na⁺ | —CN | 4 |
| 2 | H | (R)—CH(OH)CH₃ | —Na⁺ | —CN | 7 |
| 3 | H | (R)—CH(OH)CH₃ | —Na⁺ | —CN | 8 |
| 3 | H | (R)—CH(OH)CH₃ | —Na⁺ | —CN | 9 |
| 3 | H | (R)—CH(OH)CH₃ | —Na⁺ | —CN | 10 |
| 2 | H | (R)—CH(OH)CH₃ | —Na⁺ | —CHO | 4 |
| 3 | H | (R)—CH(OH)CH₃ | —Na⁺ | —CHO | 6 |
| 2 | H | (R)—CH(OH)CH₃ | —Na⁺ | —CHO | 7 |
| 3 | H | (R)—CH(OH)CH₃ | —Na⁺ | —CHO | 8 |
| 2 | H | (R)—CH(OH)CH₃ | —Na⁺ | —CHO | 9 |
| 2 | H | (R)—CH(OH)CH₃ | —Na⁺ | —CHO | 10 |
| 2 | H | (R)—CH(OH)CH₃ | —Na⁺ | —CONH₂ | 4 |
| 3 | H | (R)—CH(OH)CH₃ | —Na⁺ | —CONH₂ | 7 |
| 3 | H | (R)—CH(OH)CH₃ | —Na⁺ | —CONH₂ | 8 |
| 2 | H | (R)—CH(OH)CH₃ | —Na⁺ | —CONH₂ | 9 |
| 3 | H | (R)—CH(OH)CH₃ | —Na⁺ | —CONH₂ | 10 |
| 2 | H | (R)—CH(OH)CH₃ | —Na⁺ | —CH=NOH | 4 |
| 2 | H | (R)—CH(OH)CH₃ | —Na⁺ | —CH=NOH | 7 |
| 2 | H | (R)—CH(OH)CH₃ | —Na⁺ | —CH=NOH | 8 |
| 2 | H | (R)—CH(OH)CH₃ | —Na⁺ | —CH=NOH | 9 |
| 3 | H | (R)—CH(OH)CH₃ | —Na⁺ | —CH=NOH | 10 |
| 3 | H | (R)—CH(OH)CH₃ | —Na⁺ | —CH₂OH | 7 |
| 3 | H | (R)—CH(OH)CH₃ | —Na⁺ | —CH₂OH | 9 or |
| 2 | H | (R)—CH(OH)CH₃ | —Na⁺ | — | —.— — |

7. The compound according to claim 1, wherein the structural formula is

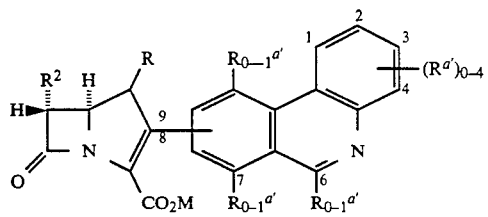

and the substituents R^{a}, where R^{a'} is R^{a} when it is not hydrogen, R, R² and M and the point of attachment of the carbapenem to the phenanthridine ring are as defined in Table II below:

TABLE II

| Att pt | R | R² | M | R^{a'} | R^{a'} position |
|---|---|---|---|---|---|
| 9 | —H | (R)—CH(OH)CH₃ | —Na⁺ | —OCH₃ | 7, 3 |
| 8 | —H | (R)—CH(OH)CH₃ | —Na⁺ | —OCH₂CO₂Me | 10 |
| 8 | —H | (R)—CH(OH)CH₃ | —H | —OCH₂CH₂OH | 3 |
| 9 | —H | (R)—CH(OH)CH₃ | —K⁺ | —CF₃ | 4 |
| 9 | —H | (R)—CH(OH)CH₃ | —Na⁺ | —F | 3 |
| 8 | —H | (R)—CH(OH)CH₃ | —Na⁺ | —Cl | 3 |
| 8 | —H | (R)—CH(OH)CH₃ | —Na⁺ | —Br | 4 |
| 9 | —H | (R)—CH(OH)CH₃ | —K⁺ | —F | 7, 4, 3 |
| 8 | —H | (R)—CH(OH)CH₃ | —Na⁺ | —OH | 3, 4 |
| 8 | —CH₃ | (R)—CH(OH)CH₃ | —H | —OCOCH₃ | 4 |
| 9 | —H | (R)—CH(OH)CH₃ | —Na⁺ | —OCONH₂ | 4 |
| 9 | —H | (R)—CH(OH)CH₃ | —Na⁺ | —SCH₃ | 7 |
| 9 | —H | (R)—CH(F)CH₃ | —Na⁺ | —SOCH₃ | 7 |
| 8 | —H | (R)—CH(OH)CH₃ | —K⁺ | —SO₂CH₃ | 3 |
| 8 | —H | (R)—CH(OH)CH₃ | —Na⁺ | —SCH₂CH₂OH | 3 |
| 9 | —H | (R)—CH(OH)CH₃ | —Na⁺ | —SOCH₂CH₂OH | 4 |
| 9 | —H | (R)—CH(OH)CH₃ | —Na⁺ | —SCH₂CONH₂ | 3 |
| 8 | —H | (R)—CH(OH)CH₃ | —Na⁺ | —SO₂NH₂ | 3 |
| 9 | —H | (R)—CH(OH)CH₃ | —Na⁺ | —SO₂N(CH₃)₂ | 4, 3 |
| 9 | —H | —CF₂CH₃ | —K⁺ | —NHCHO | 4, 3 |
| 8 | —H | (R)—CH(OH)CH₃ | —Na⁺ | —NHCOCH₃ | 6 |
| 8 | —H | (R)—CH(OH)CH₃ | —H | —NHCO₂CH₃ | 3 |
| 8 | —H | (R)—CH(OH)CH₃ | —Na⁺ | —NHSO₂CH₃ | 4 |
| 9 | —H | (R)—CH(F)CH₃ | —Na⁺ | —CN | 6 |
| 8 | —H | (R)—CH(F)CH₃ | —K⁺ | —CHO | 3 |

TABLE II-continued

| Att pt | R | R² | M | Rᵃ' | Rᵃ' position |
|---|---|---|---|---|---|
| 9 | —H | (R)—CH(OH)CH₃ | —K⁺ | —COCH₃ | 4 |
| 9 | —H | (R)—CH(OH)CH₃ | —Na⁺ | —COCH₂OH | 3 |
| 8 | —CH₃ | (R)—CH(OH)CH₃ | —Na⁺ | —CH=NOH | 3 |
| 8 | —H | (R)—CH(OH)CH₃ | —Na⁺ | —CH=NOCH₃ | 3 |
| 8 | —CH₃ | (R)—CH(OH)CH₃ | —H | —CH=NOCH₂CO₂Me | 3 |
| 9 | —H | (R)—CH(OH)CH₃ | —Na⁺ | —CH=NOCMe₂CO₂Me | 6 |
| 9 | —H | (R)—CH(OH)CH₃ | —Na⁺ | —CH=NOCMe₂CO₂Me | 3 |
| 8 | —H | (R)—CH(OH)CH₃ | —K⁺ | —CO₂CH₂CH₂OH | 4 |
| 8 | —H | (R)—CH(F)CH₃ | —Na⁺ | —CONH₂ | 3, 2 |
| 8 | —H | (R)—CH(OH)CH₃ | —Na⁺ | —CONHCH₃ | 2 |
| 9 | —H | (R)—CH(OH)CH₃ | —Na⁺ | —CON(CH₃)₂ | 1 |
| 9 | —H | (R)—CH(OH)CH₃ | —Na⁺ | —CONHCH₂CN | 7 |
| 8 | —H | (R)—CH(OH)CH₃ | —Na⁺ | —CONHCH₂CONH₂ | 3 |
| 8 | —H | (R)—CH(OH)CH₃ | —Na⁺ | —CONHCH₂CO₂Me | 4 |
| 9 | —H | (R)—CH(OH)CH₃ | —Na⁺ | —CONHOH | 2 |
| 9 | —H | (R)—CH(OH)CH₃ | —Na⁺ | —CONHOCH₃ | 2 |
| 8 | —H | (R)—CH(OH)CH₃ | —Na⁺ | -tetrazolyl | 3 |
| 9 | —H | (R)—CH(OH)CH₃ | —Na⁺ | —CO₂Me | 3 |
| 9 | —H | (R)—CH(OH)CH₃ | —Na⁺ | —SCF₃ | 7 |
| 8 | —H | (R)—CH(OH)CH₃ | —H | —PO₃MeH | 3 |
| 8 | —H | (R)—CH(OH)CH₃ | —Na⁺ | —CONHSO₂Ph | 1 |
| 8 | —H | (R)—CH(OH)CH₃ | —Na⁺ | —CONHSO₂NH₂ | 4 |
| 8 | —H | (R)—CH(OH)CH₃ | —K⁺ | —SO₃Me | 3 |
| 9 | —H | (R)—CH(OH)CH₃ | —Na⁺ | —SO₂NHCN | 3 |
| 8 | —H | (R)—CH(F)CH₃ | —Na⁺ | —SO₂NHCONH₂ | 3 |
| 9 | —H | (R)—CH(OH)CH₃ | —Na⁺ | —CH=CHCN | 3 |
| 8 | —H | (R)—CH(OH)CH₃ | —Na⁺ | —CH=CHCONH₂ | 3 |
| 8 | —H | (R)—CH(OH)CH₃ | —Na⁺ | —CH=CHCO₂Me | 3 |
| 9 | —H | (R)—CH(OH)CH₃ | —Na⁺ | —C≡C—CONH₂ | 3 |
| 9 | —CH₃ | (R)—CH(OH)CH₃ | —Na⁺ | —C≡C—CN | 4 |
| 9 | —H | (R)—CH(OH)CH₃ | —K⁺ | —CH₂OH | 6 |
| 8 | —H | (R)—CH(OH)CH₃ | —Na⁺ | —CH₂N₃ | 3 |
| 8 | —H | (R)—CH(OH)CH₃ | —Na⁺ | —CH₂CO₂Me | 3 |
| 9 | H | (R)—CH(OH)CH₃ | —Na⁺ | —CN | 7 |
| 8 | H | (R)—CH(OH)CH₃ | —Na⁺ | —CN | 4 |
| 8 | H | (R)—CH(OH)CH₃ | —Na⁺ | —CN | 3 |
| 9 | H | (R)—CH(OH)CH₃ | —Na⁺ | —CN | 2 |
| 9 | H | (R)—CH(OH)CH₃ | —Na⁺ | —CN | 1 |
| 9 | H | (R)—CH(OH)CH₃ | —Na⁺ | —CHO | 7 |
| 8 | H | (R)—CH(OH)CH₃ | —Na⁺ | —CHO | 6 |
| 8 | H | (R)—CH(OH)CH₃ | —Na⁺ | —CHO | 4 |
| 8 | H | (R)—CH(OH)CH₃ | —Na⁺ | —CHO | 3 |
| 9 | H | (R)—CH(OH)CH₃ | —Na⁺ | —CHO | 2 |
| 8 | H | (R)—CH(OH)CH₃ | —Na⁺ | —CHO | 1 |
| 9 | H | (R)—CH(OH)CH₃ | —Na⁺ | —CONH₂ | 7 |
| 8 | H | (R)—CH(OH)CH₃ | —Na⁺ | —CONH₂ | 4 |
| 8 | H | (R)—CH(OH)CH₃ | —Na⁺ | —CONH₂ | 3 |
| 8 | H | (R)—CH(OH)CH₃ | —Na⁺ | —CONH₂ | 2 |
| 8 | H | (R)—CH(OH)CH₃ | —Na⁺ | —CONH₂ | 1 |
| 9 | H | (R)—CH(OH)CH₃ | —Na⁺ | —CH=NOH | 7 |
| 8 | H | (R)—CH(OH)CH₃ | —Na⁺ | —CH=NOH | 4 |
| 8 | H | (R)—CH(OH)CH₃ | —Na⁺ | —CH=NOH | 3 |
| 8 | H | (R)—CH(OH)CH₃ | —Na⁺ | —CH=NOH | 2 |
| 9 | H | (R)—CH(OH)CH₃ | —Na⁺ | —CH=NOH | 1 |
| 9 | H | (R)—CH(OH)CH₃ | —Na⁺ | —CH₂OH | 4 |
| 9 | H | (R)—CH(OH)CH₃ | —K⁺ | —CH₂OH | 2 |
| 8 | H | (R)—CH(OH)CH₃ | —Na⁺ | — | —, — |

8. A compound according to claim 1 wherein the structural formula is:

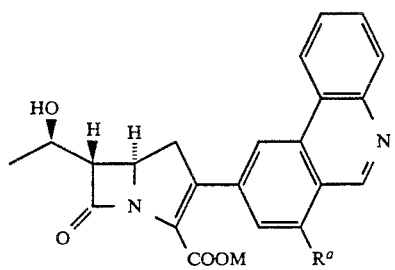

and M is Na⁺ or K⁺ and the Rᵃ substituent is selected from CH₂OH, CO₂CH₃, CONH₂, Cl, Cn, CHO, SCH₃, SCH₂CH₂OH and SO₂CH₃.

9. A compound according to claim 1 wherein the structural formula is:

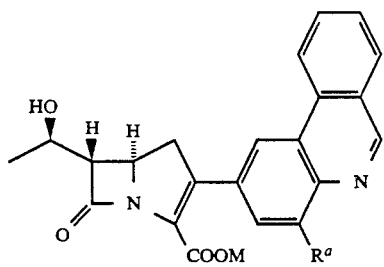

and M is Na+ or K+ and the $R^a$ substituent is selected from $CH_2OH$, $CO_2CH_3$, $CONH_2$, Cl, CN, CHO, $SCH_3$, $SCH_2CH_2OH$ and $SO_2CH_3$.

10. A compound which is selected from the group which consists of:

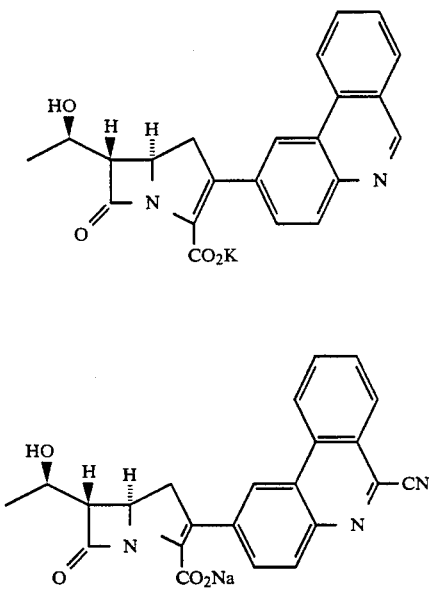

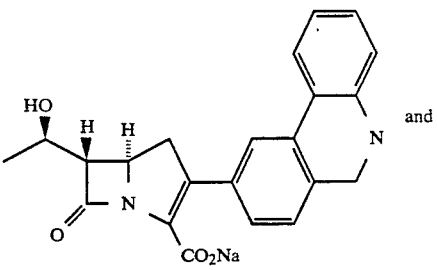

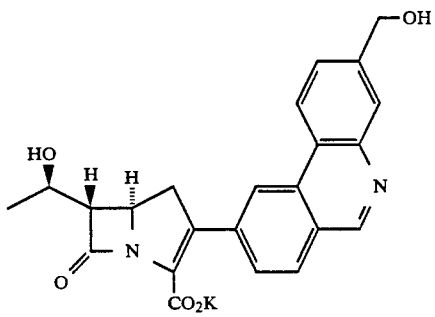

11. A pharmaceutical composition for antibacterial use comprising an antibacterially effective amount of a compound of claim 1 and a pharmaceutically acceptable carrier.

12. A method of treating bacterial infections in human or animal subjects in need of such treatment comprising administering to such subject an anti-bacterially effective amount of a compound of claim 1.

13. A pharmaceutical composition for antibacterial use comprising an antibacterially effective amount of a compound of claim 1, an inhibitorily effective amount of a dehydropeptidase (DHP) inhibitor, and optionally, a pharmaceutically acceptable carrier.

14. A pharmaceutical composition according to claim 13, wherein the DHP inhibitor is 7-(L-2-amino-2-carboxyethyl thio)-2-(2,2-dimethylcyclopropanecarboxamide)-2-heptenoic acid.

15. A method of treating bacterial infections in human or animal subjects in need of such treatment comprising coadministering to such subject an antibacterially effective amount of a compound of claim 1 and an inhibitorily effective amount of a DHP inhibitor.

16. The method according to claim 15, wherein the DHP inhibitor is 7-(L-2-amino-2-carboxyethylthio)-2-(2,2-dimethylcyclopropanecarboxamide)-2-heptenoic acid.

* * * * *